United States Patent [19]

Tran

[11] Patent Number: 4,822,339
[45] Date of Patent: Apr. 18, 1989

[54] THERAPEUTIC AGENT DELIVERY SYSTEM AND METHOD

[75] Inventor: Loi H. Tran, Wheaton, Ill.

[73] Assignee: Controlled Release Technologies, Inc., Batavia, Ill.

[21] Appl. No.: 62,959

[22] Filed: Jun. 16, 1987

Related U.S. Application Data

[63] Continuation-in-part of Ser. No. 679,128, Dec. 6, 1984, Pat. No. 4,715,850.

[51] Int. Cl.⁴ .............................................. A61M 5/00
[52] U.S. Cl. ...................................... 604/82; 604/246; 604/891.1
[58] Field of Search ......... 604/82, 56, 65-67, 604/80-86, 114, 126, 245, 246, 890-898; 128/625

[56] References Cited

U.S. PATENT DOCUMENTS

| | | | |
|---|---|---|---|
| 3,923,426 | 12/1975 | Theeuwes | 417/48 |
| 3,976,068 | 8/1976 | Lundquist | 604/52 |
| 4,140,121 | 2/1979 | Kuhl et al. | 604/891.1 |
| 4,149,957 | 4/1979 | Gibson et al. | 204/301 |
| 4,180,771 | 12/1979 | Guckel | 128/635 |
| 4,233,973 | 6/1980 | Shukla | 604/84 |
| 4,436,094 | 3/1984 | Cerami | 128/635 |
| 4,439,183 | 3/1984 | Theeuwes | 604/85 |
| 4,441,538 | 4/1984 | Larkin et al. | 604/415 |
| 4,484,909 | 11/1984 | Uruhart et al. | 604/82 |
| 4,492,622 | 1/1985 | Kuypers | 128/635 |
| 4,540,403 | 9/1985 | Theeuwes | 604/85 |

Primary Examiner—Stephen C. Pellegrino
Attorney, Agent, or Firm—Olson & Hierl

[57] ABSTRACT

A method and apparatus for controllably administering one or more therapeutic agents to a patient is disclosed. The method and apparatus uses an electromotive force between an anode and a cathode to cause at least one therapeutic agent to migrate through a semipermeable ion selective membrane. The therapeutic agent is then delivered to a patient.

26 Claims, 10 Drawing Sheets

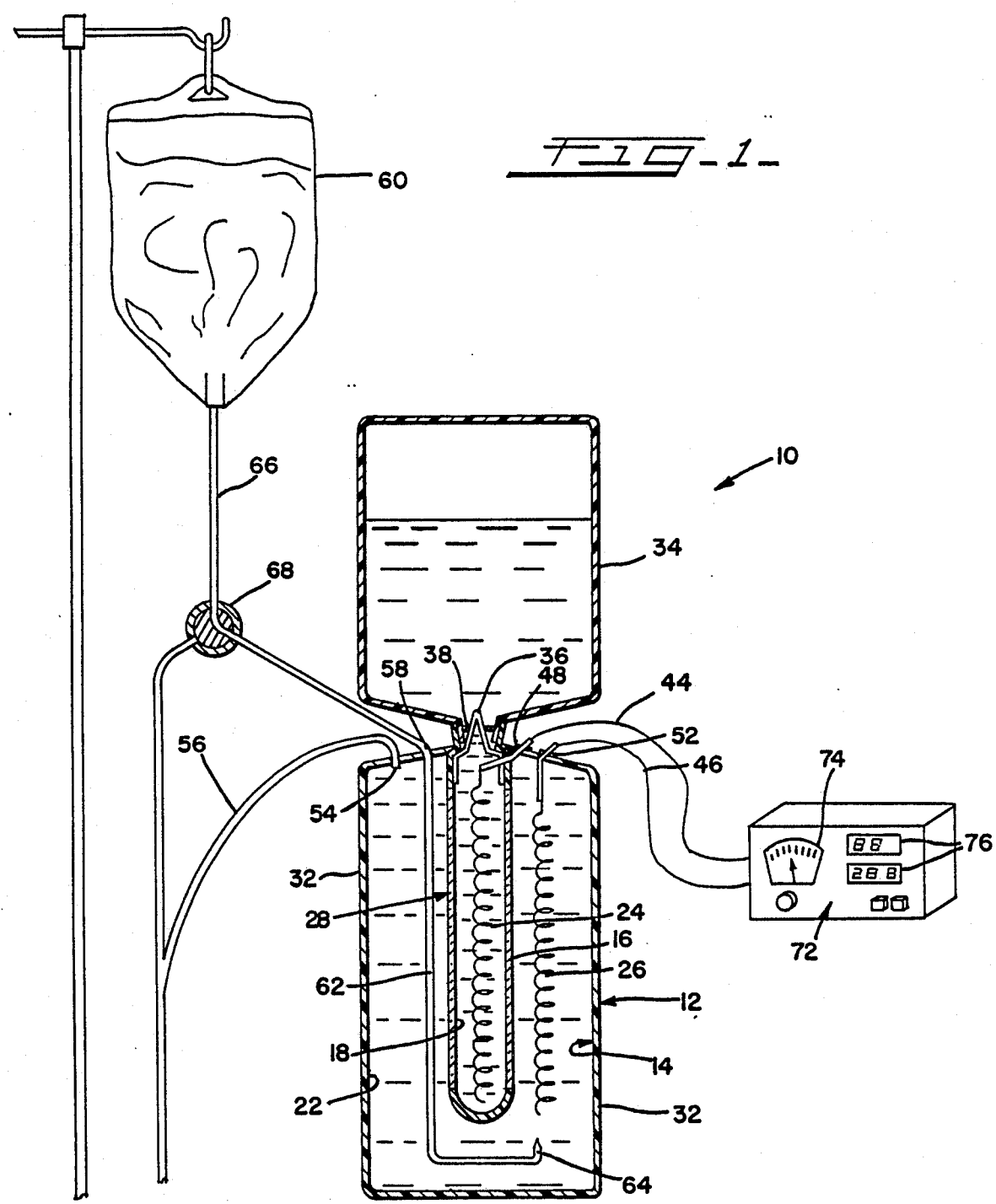

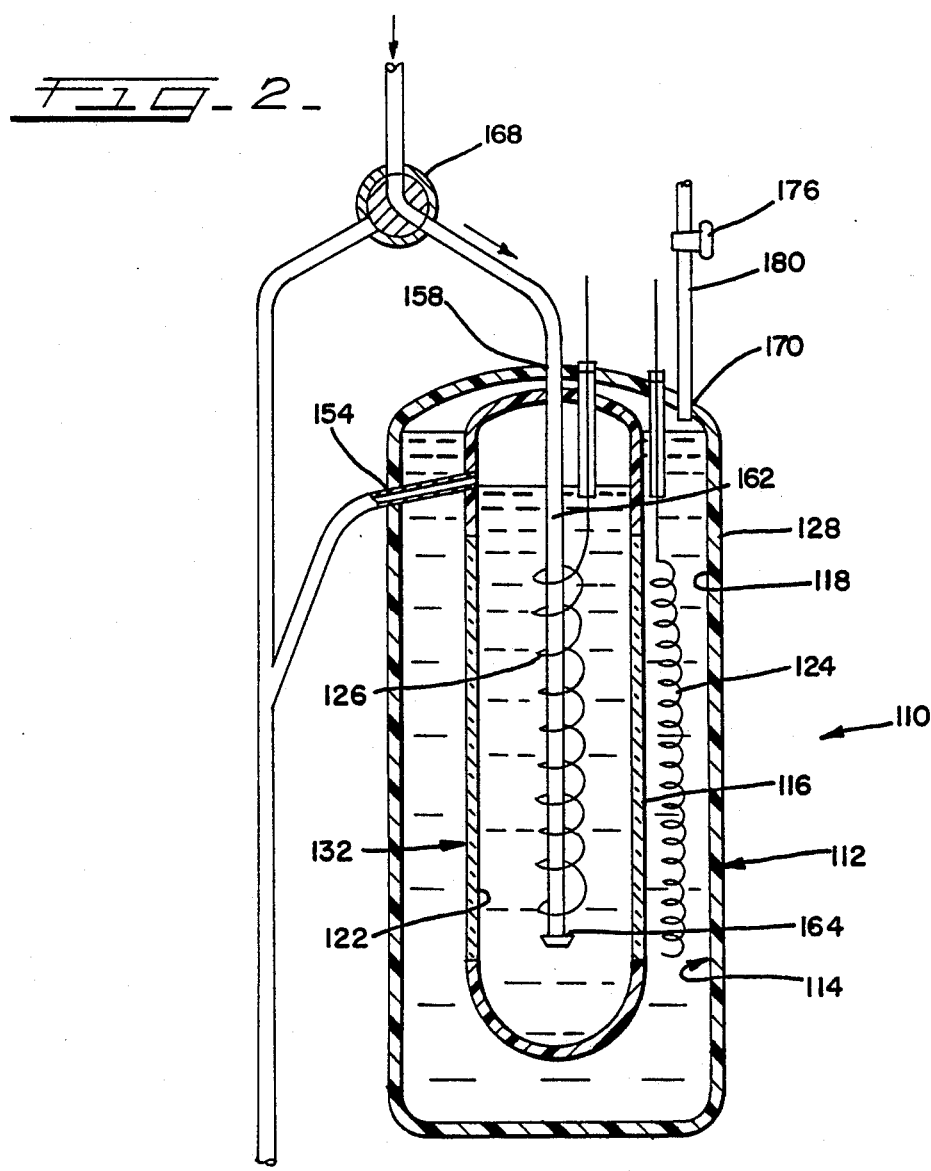
FIG_2
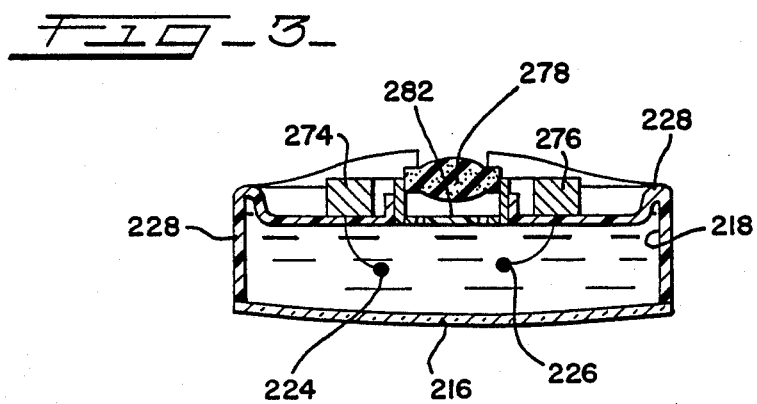
FIG_3

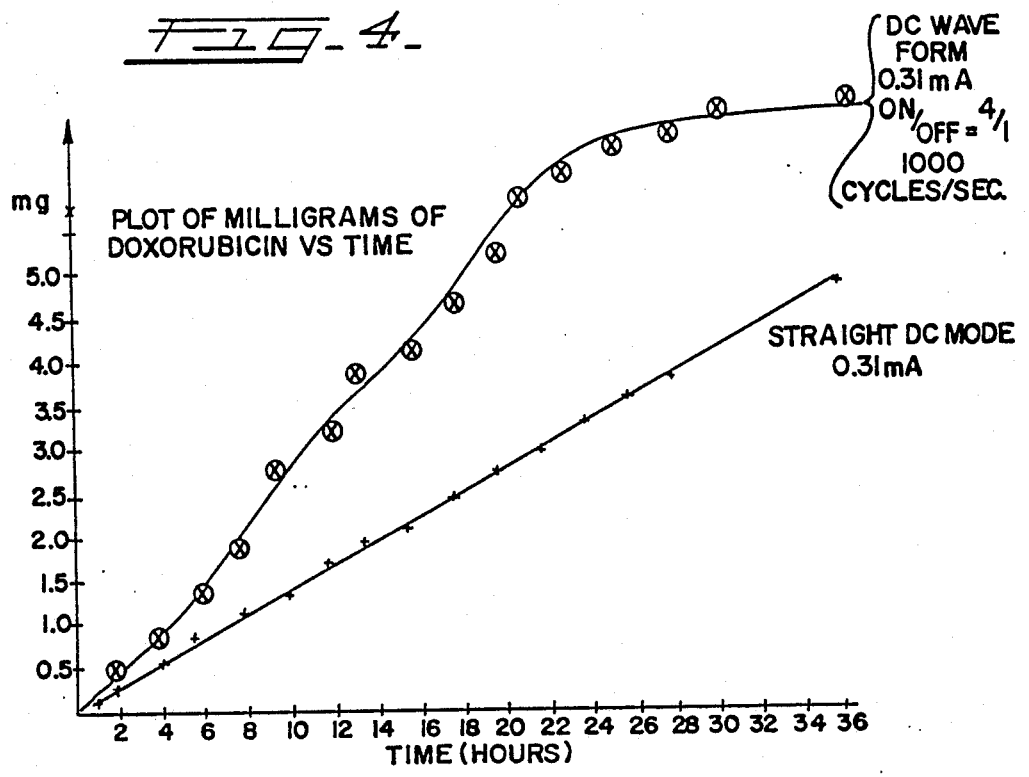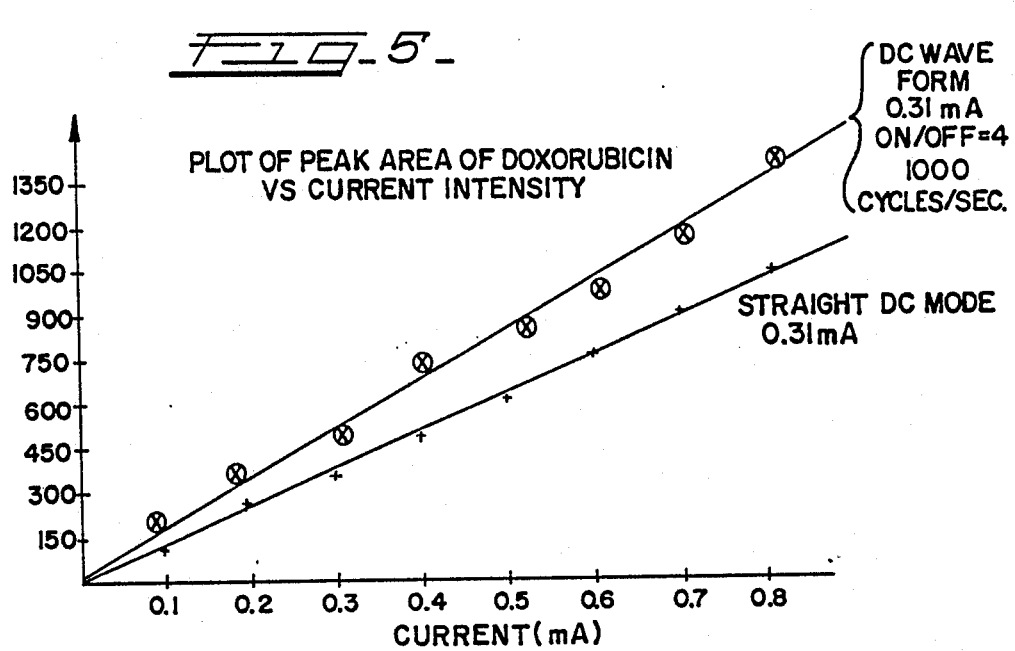

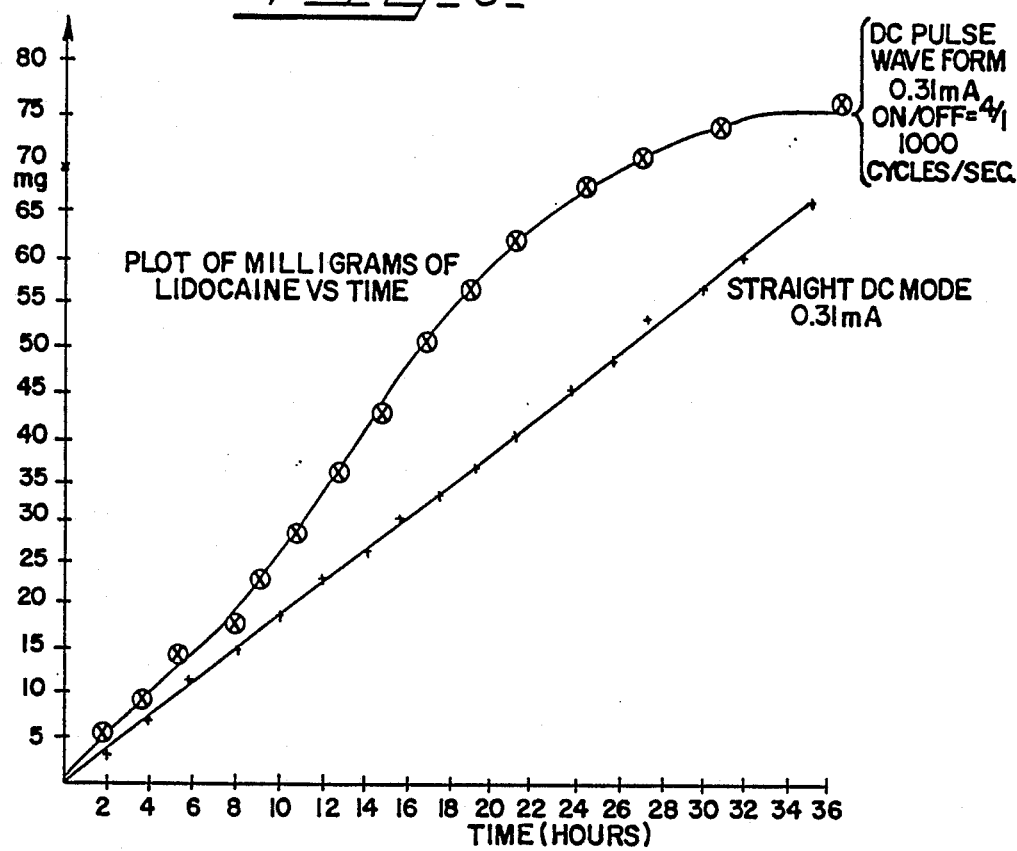
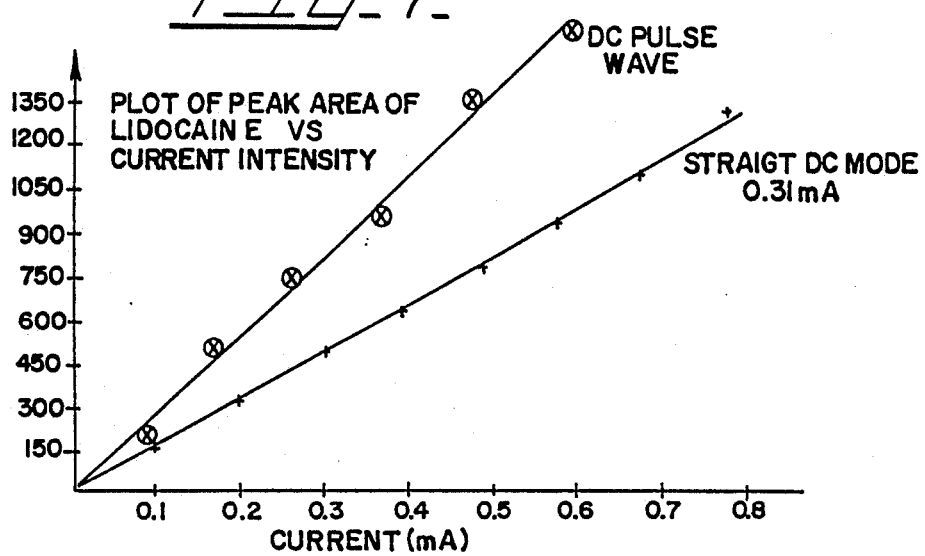

PLOT OF MILLIGRAMS OF CLONIDINE VS TIME

PLOT OF PEAK AREA VS CURRENT INTENSITY (CLONIDINE)

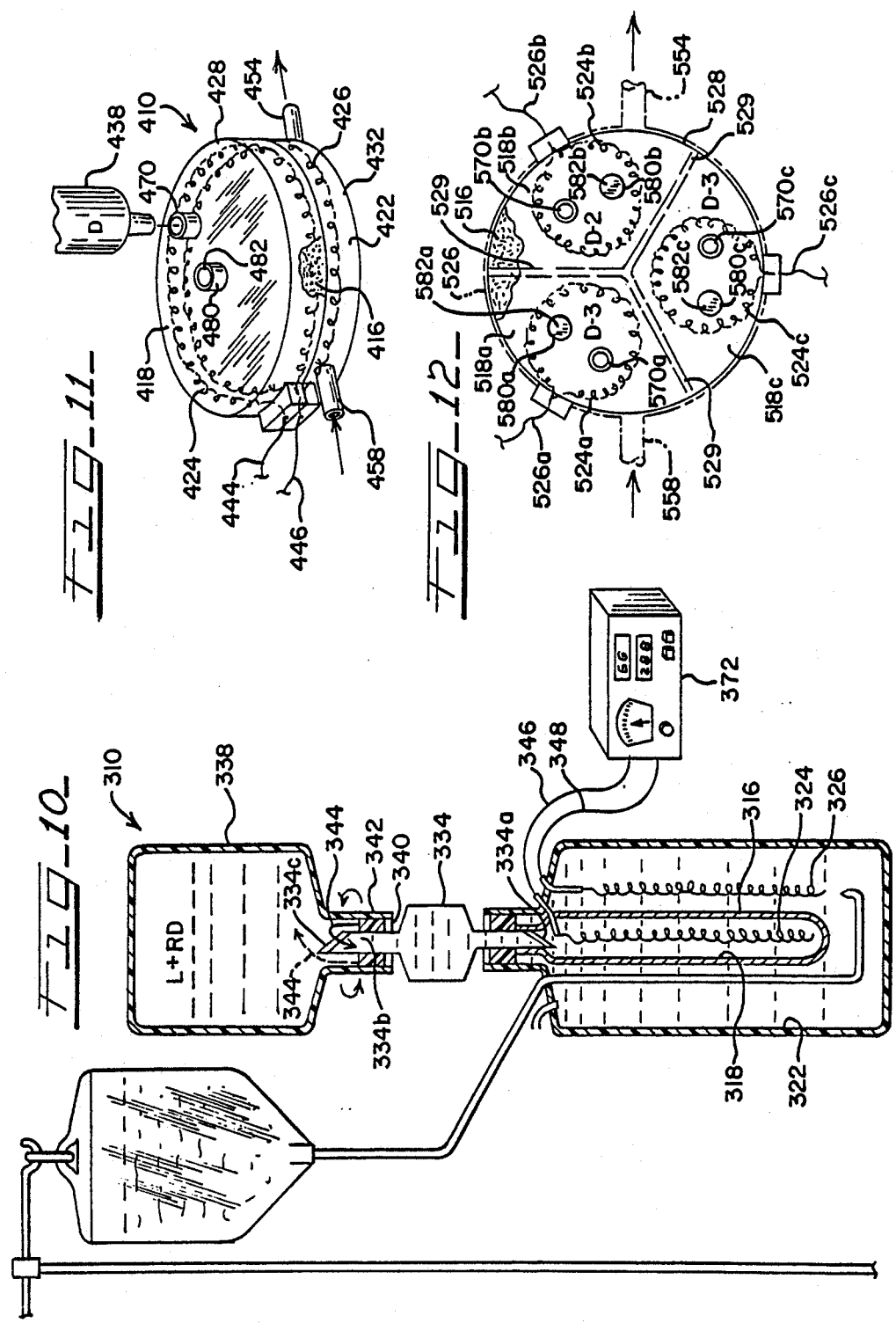

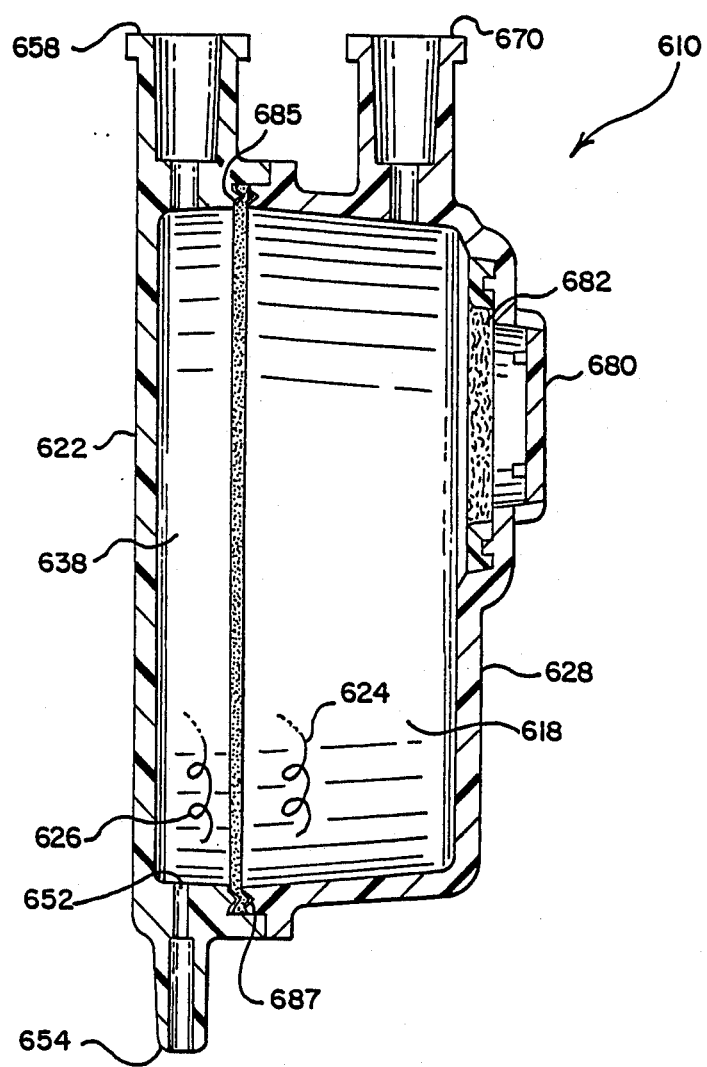

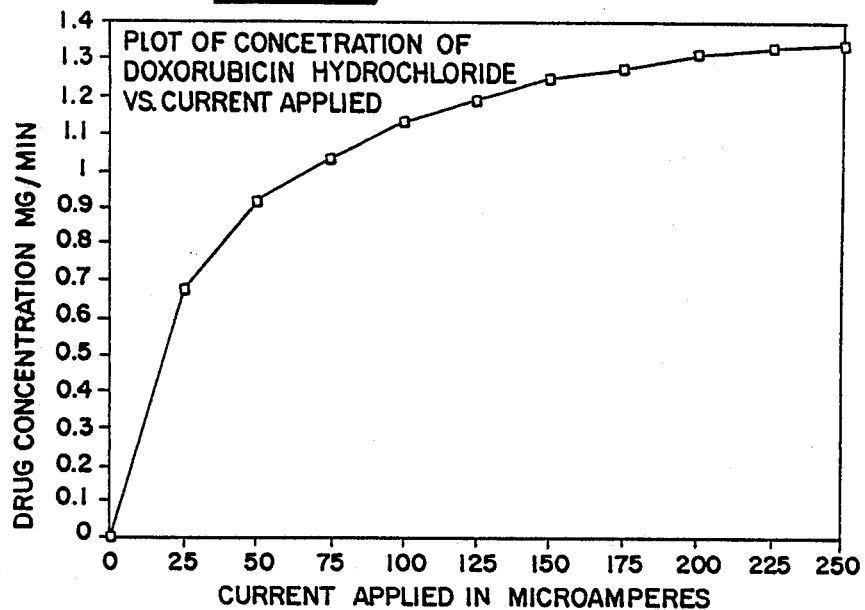
FIG-16-
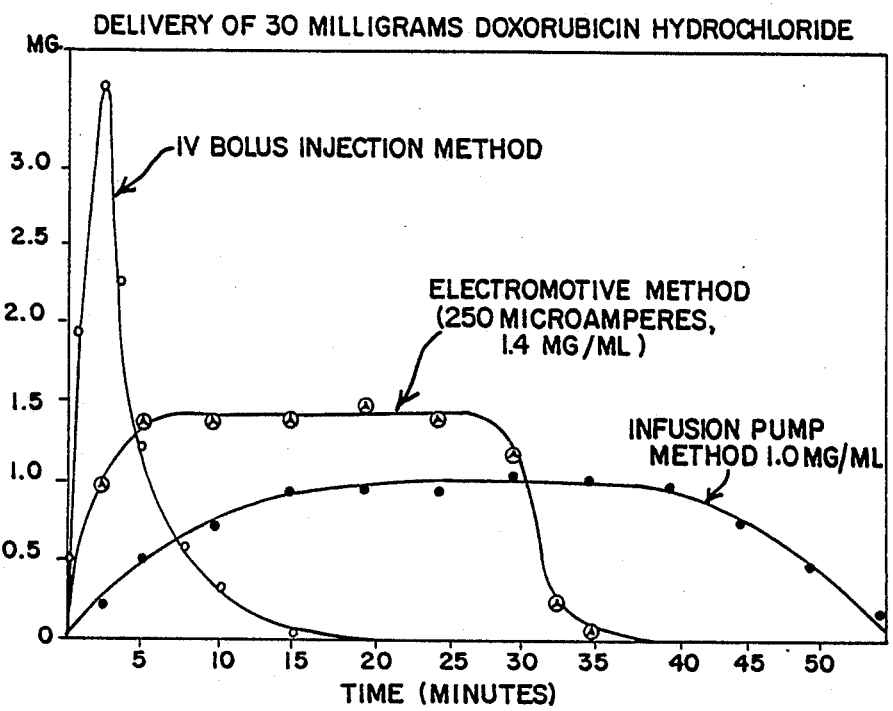
FIG-17-

THERAPEUTIC AGENT DELIVERY SYSTEM AND METHOD

This application is a continuation-in-part and division of co-pending application Ser. No. 679,128 filed Dec. 6, 1984 now U.S. Pat. No. 4,715,850, which is incorporated by reference.

TECHNICAL FIELD OF THE INVENTION

The present invention relates to systems and methods for administering a therapeutic agent to a patient by means of an electromotive force between electrodes.

BACKGROUND OF THE INVENTION

It is quite common to administer a drug to a patient over time by first diluting the drug in a liquid vehicle such as saline. Generally, the drug is mixed with the liquid vehicle, and the resulting solution is then administered intravenously to the patient. However, once mixed, the concentration of the drug in the solution remains relatively constant and only the administration rate of the solution can be adjusted.

To allow changes in drug concentrations, devices that mix the drug with the liquid vehicle have been developed. These devices use roller clamps to separately control the drip rates of the drug and liquid vehicle into a mixing chamber. Once the roller clamps are set, the mixing ratio remains the same until someone changes the settings. Even this type of system does not allow for the periodic automatic administration of a bolus of drug.

Other devices provide for the sequential administration of a drug followed by a physiologically tolerable liquid carrier such as saline. Such systems provide for automatic switching to the saline after the drug has been administered. Unfortunately, none of these devices provide for timing or variable control of the administration of the drug to the patient.

It is sometimes desirable to administer a bolus of a particular drug at given times to the patient. Present devices for such administration rely on electrical timer systems that operate mechanical valves. The rates and time of drug administration are set in the device, and the valves are opened and closed automatically. However, such devices are relatively complicated and rely on the operation of a mechanical valve having the inherent disadvantage of possible failure through valve malfunction.

What is needed is a system and method for delivering a therapeutic agent to a patient which is easily adjustable without the need of mechanical means. Such a device should allow for the easy control of administration rates as well as times of administration. The present invention meets these desires.

SUMMARY OF THE INVENTION

The present invention is a system and method for delivering one or more therapeutic agents to a patient by use of an electromotive force between an anode and a cathode. Suitable therapeutic agents include active agents such as drugs or hormones, or active agents coupled to an appropriate carrier. Either the active agent or the carrier is in an ionic form such as a pharmaceutically acceptable salt. For example, such a salt can be represented by the formula $RY^+X^-$ wherein $RY^+$ includes a cationic (positively charged) group such as $RNH^+_3$, and $X^-$ is an anionic (negatively charged) group such as $Cl^-$ or $Br^-$.

A therapeutic agent delivery apparatus of this invention comprises a housing defining a cavity which is divided by a semipermeable ion selective membrane to define at least one donor chamber adapted to receive and hold the therapeutic agent and a receiving chamber adapted to receive the therapeutic agent from at least the one identified donor chamber through the membrane. Electrodes, an anode and a cathode, are in communication with each chamber of the cavity. When an electromotive force of a sufficient amount is applied between the electrodes, at least a portion of the therapeutic agent migrates from the donor chamber through the semipermeable membrane to the receiving chamber and is delivered to the patient. The rate of therapeutic agent delivery is a function of the current between the electrodes. Consequently, when the electromotive force is no longer applied between an anode and a cathode, no further therapeutic agent is delivered from the donor chamber to the receiving chamber, and remaining therapeutic agent is retained in the donor chamber.

In one preferred embodiment of the invention, one electrode is in communication with at least one donor chamber and the other electrode is placed on the other side of the semipermeable membrane in communication with the receiving chamber. The membrane is preferably circular and captured between two housings. The electrode in communication with one identified donor chamber will have the same charge as the desired retained ionized therapeutic agent. For a hydrochloride salt, the ionized therapeutic agent has a positive charge and this electrode is an anode.

In another preferred embodiment, a semipermeable ion selective membrane separates a multiplicity of donor chambers in a first housing from a common receiving chamber in a second housing. The first housing carries a multiplicity of electrodes such that each donor chamber carries an electrode in communication therewith. A driving electromotive force across the membrane is generated between a first electrode in one identified donor chamber containing the therapeutic agent and the electrode in the receiving chamber to controllably pass therapeutic agent through the membrane for delivery to a patient. Alternatively, a driving electromotive force can be simultaneously, serially, or sequentially generated between the electrode in the receiving chamber and the various electrodes in the donor chambers to deliver more than one therapeutic agent from different donor chambers.

The semipermeable membrane is ion selective to allow the charged therapeutic agent, but not its oppositely charged corresponding ion, to pass through the membrane. In the case of a positively charged therapeutic agent such as $RY^{30}$, the membrane allows the passage of cations but is substantially impermeable to anions such as chloride ions. Even though the therapeutic agent ions could diffuse through the semipermeable membrane when there is no electromotive force between the electrodes, there is no net flow of agent because of the need to maintain an electrochemical balance between donor and receiving chambers. Thus, if an excess of the cationic therapeutic agent were to diffuse through the membrane, the donor chamber would have a net negative charge and the agent would be drawn back to maintain the necessary electrochemical balance. The anionic chloride ions cannot also pass through the membrane with the agent.

In one aspect, the membrane serves as a porous filter for particulates and bacteria and is used to regulate and control the amount of drug administered by serving as a barrier over which the ionic therapeutic species have to pass in order to go from one side of the membrane to the other side. Even though these ionic species or charged particles are smaller than the pores of the membrane, they are normally prevented from crossing the membrane. The membrane has a surface charge opposite to that of the charged particle, by a phenomenon known as zeta potential (Vo) mechanism or electrostatic attraction. However, the zeta potential can be overcome by applying an electropotential field ($V^*$) so that $V^* > Vo$.

Thus, when an electromotive force or charge is placed between the anode and the cathode, the ionized therapeutic agent migrates through the semipermeable membrane. The externally applied charge negates the necessity for maintaining an electrical balance between the ions in the two chambers and provides a driving force for the cationic agent toward the cathode in the receiving chamber.

After the therapeutic agent enters the receiving chamber, it can be delivered to the patient by appropriate delivery means. One preferred form of delivery is to pass a liquid vehicle such as saline or dextrose through the receiving chamber to mix with the therapeutic agent and deliver the mixture to the patient intravenously.

Still another preferred embodiment permits reconstituted therapeutic agent to be delivered from an external reservoir mounted in fluid communication with at least one donor chamber of a system of this invention. Reconstituted therapeutic agent means a therapeutic agent that is normally sold in substantially solid form, such as a powder, to be dispersed in a physiologically tolerable liquid for administration to a patient. In this instance, a portion or all of the substantially solid therapeutic agent is initially retained in a therapeutic agent reservoir having two sealable openings. The first opening includes a removable first sealing means and is adapted for releasable connection in fluid communication with a donor chamber on removing the sealing means. The second opening includes a puncturable second sealing means, and is adapted for fluid communication with a removable container retaining a physiologically tolerable liquid and including a piercing means for the second sealing means.

In a method aspect of this embodiment, the substantially solid therapeutic agent is reconstituted by mating the second opening of the therapeutic agent reservoir with the container and in contact with the container's piercing means. On piercing the second sealing means, the therapeutic agent is received in the container and dispersed in the liquid. All or a portion of the reconstituted therapeutic agent can be retained in the container until needed in a substantially sterile manner. When needed, the first sealing means is removed from the first opening and that opening is then mounted in fluid communication with the identified donor chamber of a therapeutic agent delivery system of this invention.

In another preferred embodiment of the present invention, both the anode and cathode are in communication with the donor chamber. The semipermeable membrane in this instance is substantially impermeable to the ionic form of the therapeutic agent, but is permeable to the non-ionic form of the therapeutic agent. One example of such a membrane is a hydrophobic membrane. The therapeutic agent is placed within the donor chamber in its ionic form where it is retained by the membrane. When an electromotive force is placed between the anode and cathode, the therapeutic agent changes from its ionic form to a non-ionic form which then passes through the membrane to be administered to the patient. In the example given above, $RY^+X^-$ is converted to RY, with $X^-$ combining with another ion such as silver $Ag^+$ from an anode.

The embodiments discussed above permit easy control of the rate and amount of one or more therapeutic agents which are administered to a patient. The rate of administration is a function of the current between the anode and the cathode while the total amount administered is a function of the rate and time that an electromotive force is applied between the anode and the cathode. This provides for easy control without the necessity of a complicated valve mechanism.

Because an electrical current operates the present invention, electrical control is easily accomplished by an appropriate control means such as a microprocessor associated with power source means such as a battery. The system also has the inherent advantage that should there be any form of power interruption, there is no longer a potential between the electrodes and no therapeutic agent is administered to the patient.

Numerous other advantages and features of the present invention will become readily apparent to those skilled in the art from the following detailed description of the preferred embodiments of the invention, the drawings, and the claims.

BRIEF DESCRIPTION OF THE DRAWINGS

FIG. 1 is an elevational view, partly in section, of an embodiment of the present invention showing a donor chamber generally located within the receiving chamber together with means for delivering the therapeutic agent to a patient;

FIG. 2 is an alternative embodiment of the present invention in which the receiving chamber is located generally within the donor chamber;

FIG. 3 is a further alternative embodiment of the present invention having two electrodes located within a donor chamber;

FIGS. 4-9 show results of studies of the present invention with the drugs doxorubicin hydrochloride, lidocaine hydrochloride, and clonidine hydrochloride;

FIG. 10 is an elevational view, partly in section, of another embodiment of the present invention for delivering reconstituted therapeutic agent showing the therapeutic agent reservoir mounted in fluid communication with the donor chamber;

FIG. 11 is a perspective view of still another embodiment of the present invention having a disc shape;

FIG. 12 is a top view of an alternate embodiment of the disc shaped device in FIG. 11 configured to have multiple donor chambers with an electrode located within each donor chamber;

FIG. 13 is an elevational view, in section, of an alternative disc-shaped embodiment in which the donor chamber is positioned in vertical parallel relationship to the receiving chamber; and FIGS. 14-19 show results of studies with the drugs aminophylline hydrochloride, doxorubicin hydrochloride and dopamine hydrochloride, delivered by a disc shaped embodiment of the type shown in FIG. 11.

DETAILED DESCRIPTION OF THE PREFERRED EMBODIMENTS

Figure 8:
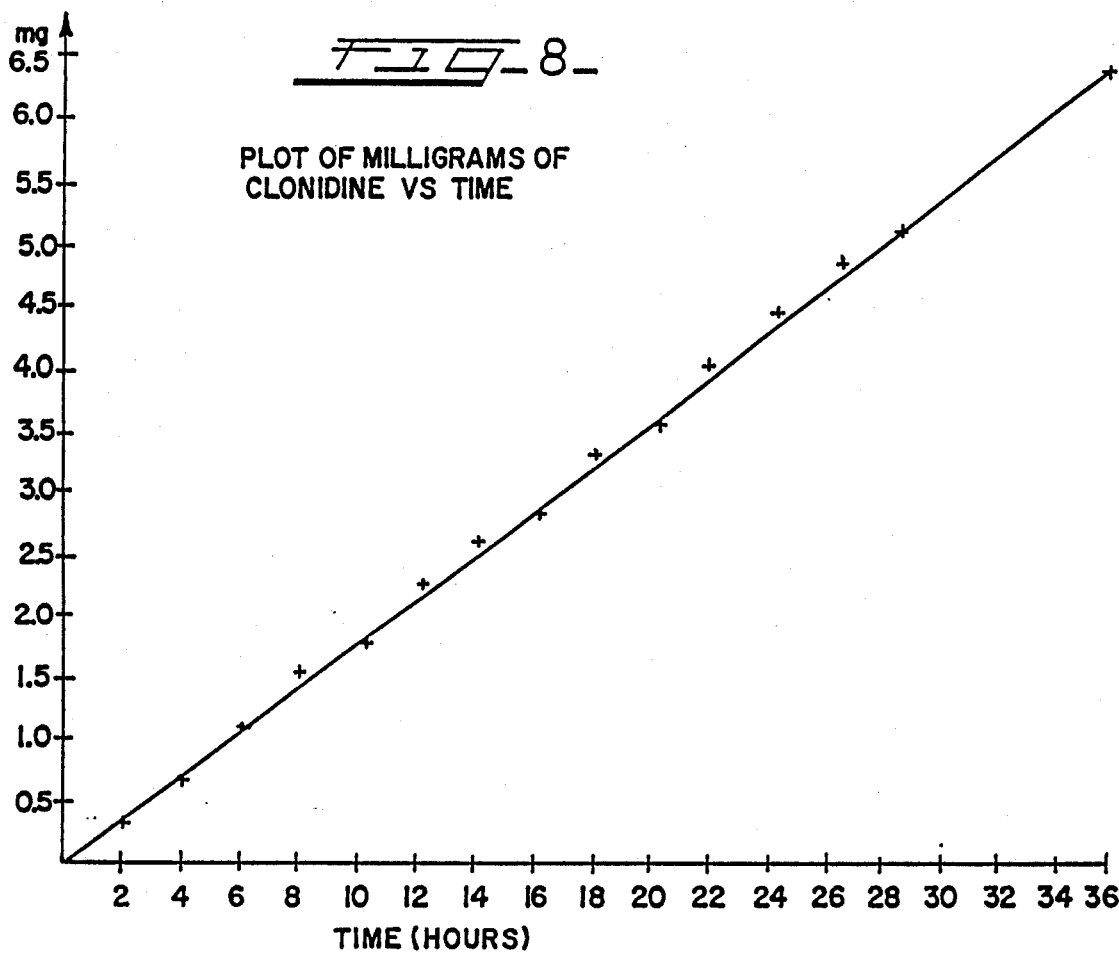

While this invention can be embodied in many different forms, there are shown in the drawings and described in detail, preferred embodiments of the present invention. The present disclosure is an exemplification of the principles of the invention and is not intended to limit the invention to the embodiments illustrated.

The present invention is a method and system for administering one or more therapeutic agents to a patient. The therapeutic agent can be almost any active agent, such as a drug or hormone, which can exist in an ionized form or any active agent, which can be coupled to a carrier that is ionizable.

Either the active agent or the carrier is in an ionic form. One such compound is a pharmaceutically acceptable salt. Such a salt can be represented by the formula $RY^+X^-$ wherein $RY^+$ includes a cationic group, such as $NH^+_3$, $NH^+_2$, or $NH^+$ and $X^-$ is an anion such as $Cl^-$ or $Br^-$. Also possible are compounds having the general formula $RY^-X^+$, such as where $Y^-$ is a carboxyl group, a sulfonate group, barbital (5,5-dimethyl barbituric acid), or a phosphamide, and $X^+$ is a physiologically tolerable cation, such as sodium, potassium, calcium or magnesium. In either case, R represents the remainder of the active agent or active agent-carrier combination. Generally, the small anion or cation (depending on the formula for the therapeutic agent, either $X^-$ or $X^+$) will not be delivered to the patient. The portion represented by $RY^+$ or $RY^-$ is the active agent or active agent coupled to a carrier and is considered the therapeutic agent which is delivered to the patient. It is this portion which carries the active agent that has the therapeutic effect.

The therapeutic agent is placed within a donor chamber in its ionic form. The donor chamber is defined in part by a semipermeable membrane. When an electromotive force above a certain minimum amount (which varies depending on the agent and membrane) is placed between an anode and a cathode, the therapeutic agent migrates through the semipermeable membrane to be delivered to the patient.

Referring to the first embodiment in FIG. 1, a device 10 of the present invention is shown with a housing means 12 defining a cavity 14 divided by a semipermeable membrane 18 into a donor chamber 18 and a receiving chamber 22. The donor chamber 18 is adapted to hold the therapeutic agent while the receiving chamber 22 is adapted to receive the therapeutic agent from the donor chamber through the membrane 16.

The housing means 12 includes a first housing 28 which defines the donor chamber 18 and a second housing 32 which defines the receiving chamber 22. As shown, the donor chamber 18 is separated from the receiving chamber 22 by the semipermeable membrane 16. The membrane 16 can be any suitable shape, such as a disc, sheet or as shown in FIG. 1, a hollow tube about 1.75 centimeters in diameter. The semipermeable membrane 16 can be considered as part of the structure which defines both the donor chamber 18 and the receiving chamber 22.

The semipermeable membrane 18 is permeable to the ionized therapeutic agent, but is substantially impermeable to an oppositely charged ion. For example, in the case of a positively charged therapeutic agent, the membrane 16 permits the passage of cations, but substantially prevents the passage of anions. The membrane 16 can be made of a microporous material having a pore size less than about 0.22 micrometers.

A variety of materials may be used to prepare membrane 16, and such materials may exhibit ion selectivity based on differentials in porosity, as well as surface charge. In such an instance, the polymeric material already bearing the desired surface charge may be fabricated into the membranes. Alternatively the pre-fabricated membrane may be subsequently treated to modify its surface charge. Suitable materials may be selected from positively charged (cationic) and negatively charged (anionic) polymers, as well as materials possessing both a positive and a negative charge.

Thus, where the desired ionized therapeutic agent is positively charged, the membrane should be negatively charged (anionic), i.e., permeable to cations and substantially impermeable to anions.

Suitable negatively charged materials for the membrane include anionic polymers, such as perfluorosulfonic acid polymers, carboxylic acid polymers such as poly(sodium methacrylate), and phosphoric acid polymers, such as poly(vinyl sodium phosphonate), polyacrylic acid and polyethylene terephthalate. One particularly preferred polymer is a perfluorosulfonic acid polymer having internal sulfonic acid groups sold by Cole Parmer of Chicago, Ill. under the trademark Spectra/Por Ion Selective Membrane. Another particularly preferred membrane is a nylon 66, modified to provide a high concentration of carboxyl functional groups at the surface of the membrane pores, sold by Pall, BioSupport Division, of New York under the trademark Carboxydyne. The manufacturer of the Pall Carboxydne membrane states that this membrane has a negative zeta potential in both basic and acidic solutions. Other suitable membranes include a cation exchange membrane sold by Asahi Glass & Co. under the trademark Selemion CSV.

Where the therapeutic agent is negatively ionized such as by ionizing a carboxyl or sulfonate group, the membrane should be positively charged (cationic), i.e., permeable to anions and substantially impermeable to cations.

Suitable positively charged materials include ion selective membranes prepared from water-insoluble cationic polymers or porous material whose pore surface charge is modified by treating with a polycation, such as a quaternary polyelectrolyte, to introduce functional quaternary ammonium, sulfonium and phosphonium groups. Quaternary cationic polyelectrolytes are preferred for this purpose.

Such cationic polyelectrolytes include: quaternary ammonium polymers such as polypyrazine, poly(vinyl trimethyl ammonium chloride), poly(N-methyl vinyl pyridinium chloride), and poly(diallyl dimethyl ammonium chloride). See generally, Hoover, *J. Macromolecular Sci.* A4, p. 1327 (1970).

A particularly preferred positively charged membrane is Nylon 66 modified by the addition of quaternary ammonium groups sold by Pall, Biosupport Division, of New York under the trademark N66 Posidyne. According to the manufacturer, a high concentration of these cationic functional groups at the pore surface of the membrane produces a positive zeta potential in both acidic and basic solutions over a pH range of 3-10.

Exemplary polymeric materials possessing a combined positive and negative charge may comprise insoluble polyelectrolyte complexes or polysalts, such as a copolymer of the polyanion, poly(sodium styrene sulfonate) and the polycation, poly(vinylbenzyltrimethylammonium chloride). Another membrane is a nylon 66 membrane having a protein-like surface populated by 50 percent amine groups and 50 percent carboxyl group sold by Pall, Biosupport Division, of New York under the trademark Ultipor N66. According to the manufacturer, this membrane is isoelectric at pH 6 and can selectively have a positive zeta potential at a pH<6 and a negative zeta potential at pH>6.

The foregoing materials are illustrative of suitable polymers that may be used in preparing membrane 16. The invention is not limited to these specific materials, but rather encompasses those materials possessing the requisite porosity and charge capability for practicing the principles of this invention.

A membrane is considered to be ion selective, therefore, if it has a higher diffusion rate for one type of ion as opposed to another. Thus, in the case of an anionic polymer, it is permeable to cations in that it allows cations to pass or migrate through the pores of the membrane, but is substantially impermeable to anions in that it substantially prevents the passage of anions. It should be kept in mind that no membrane is perfect and the passage of a certain small amount of anions is acceptable.

The device 10 also includes two electrodes, a first electrode 24 in fluid communication with the donor chamber 18 and a second electrode 26 in fluid communication with the receiving chamber 22. The electrodes are most easily placed in fluid communication with their respective chambers by being exposed within their respective chambers. In the case of a negatively ionized therapeutic agent, the first electrode 24 is a cathode while the second electrode 26 is an anode. However, for ease of description, the more common case of a positively charged ionized therapeutic agent will be given, in which case the first electrode 24 is an anode and the second electrode 26 is a cathode.

The electrodes 24 and 26 can be made of any suitable material which preferably does not chemically react with either the therapeutic agent or any liquid vehicle within the system such as saline. Suitable electrode materials include platinum, silver, carbon and gold. Silver is particularly preferred for implantable devices to avoid the production of chlorine gas by reacting the newly migrated silver ions with the excess chlorine ions to form silver chloride. As shown, the electrodes 24 and 26 are wire electrodes which are coiled to save space. Other configurations of electrodes are also possible such as flat ribbon electrodes having a high surface area. Leads 44 and 46 for the electrodes 24 and 26 are provided with appropriate seal means 48 and 52 as they enter their respective housings 28 and 32. The electrodes preferably have a surface area of about 0.50 to about 1.2 square centimeters.

In the embodiment shown in FIG. 1, the portion of the donor chamber 18 defined by the semipermeable membrane 16 is located within the receiving chamber 22. This allows for a maximizing of the surface area of the semipermeable membrane 16 between the two chambers while minimizing the overall size of the device.

A removable drug reservoir 34 can also be provided in fluid communication with first housing 28. It is preferred that the drug reservoir 34 be elevated relative to the first housing 28 so that gravity drives the therapeutic agent into the donor chamber 18 to replace that agent which has been passed through the semipermeable membrane 16 and has been administered to the patient.

As shown in FIG. 1, the first housing 28 is preferably provided with a spiked cannula 36 which pierces a septum 38 on the drug reservoir 34 as the drug reservoir is mounted on the first housing 28. This simplifies use since different types of therapeutic agents may be stored in replaceable drug reservoirs 34 and supplied as needed. This also simplifies refilling of the donor chamber 18 as the therapeutic agent is administered to the patient.

The first housing 28, second housing 32, and refillable drug reservoir 34 can be made of any suitable medical grade material. Such materials include glass, polypropylene, polyethylene, polycarbonate, acrylate and polystyrene and are preferably sterilizable and disposable for one time use.

Delivery means for delivering the therapeutic agent from the receiving chamber 22 to the patient are also provided. Such delivery means can be as simple as an outlet 54 mounted on the second housing 32 in fluid communication with the receiving chamber 22. The therapeutic agent which passes through the membrane 16 in the receiving chamber 22 can then be delivered through the outlet 54 to the patient such as by means of an appropriate flexible tubing 56. The tubing 56 can be attached to a needle or catheter (not shown) to deliver the drug intravenously.

As shown in FIG. 1, the delivery means preferably also includes an inlet 58 mounted on the first container 32 in fluid communication with the receiving chamber 22. The inlet 58 is preferably connected to a conduit 62 which extends into the receiving chamber 22 and has an opening 64 which is spaced from the outlet 54 such that the flow of liquid vehicle from the inlet to the outlet dynamically mixes with the therapeutic agent in the receiving chamber 22 before delivery to the patient. The inlet 54 can be connected to an appropriate container 60 of a physiologically tolerable liquid vehicle, such as saline, by appropriate tubing 66. A three-way valve 68 can also be provided to either direct the flow of the liquid vehicle through the device 10 or to bypass the device and deliver the liquid vehicle directly to the patient.

As shown, the electrodes 24 and 26 are connected by leads 44 and 46 to an operating unit 72 including power source means and control means. The power source means provides a direct current from either a battery or includes appropriate means for reducing the power coming from a wall outlet and also converting it to DC power. The minimum amount of electromotive force varies depending on the therapeutic agent and membrane being used. In the case of a perfluorosulfonic acid polymer as described above, a minimum voltage of about 0.3 to about 0.4 volts is needed to drive a therapeutic agent such as doxorubicin hydrochloride through the membrane. The preferred operating voltage range of the device is from about 3 volts to about 6 volts, direct current. If desired, direct current can be controlled for pulse wave form.

The control means regulates the operation of the power source and can include an appropriate timing circuit that can be set to administer the therapeutic agent for a given amount of time, to administer a certain amount of therapeutic agent at regular periodic intervals, or to even alter the amount of therapeutic agent which is given at different times.

To a certain extent, the control means can also allow the patient to control the administration of the therapeutic agent. Thus, the patient would be able to receive a pain reducing agent when necessary, but the control means would provide an override to prevent the patient from overmedicating.

As shown on the operating unit 72 in FIG. 1, an ammeter 74 forming part of the power source means indicates the delivery rate of the therapeutic agent. As discussed in more detail below, the act of therapeutic agent delivery is substantially a linear function of the current between the anode and cathode. As also shown on the operating unit 72, indicators 76 for a timing circuit form part of the control means.

Referring to FIG. 2, an alternative embodiment for a device 110 of the present invention is shown. As before, the device 110 includes a housing means 112 defining a cavity 114 and having a first housing 128 defining a donor chamber 118 and a second housing 132 defining a receiving chamber 122. Membrane 116 separates the two chambers. However, the second housing 132 is located within the first housing 128, the reverse of the device 10 shown in FIG. 1. As shown, the two housings 128 and 132 are substantially cylindrical and coaxial.

The first electrode 124 and the second electrode 126 are substantially as before. The delivery means includes inlet 158, conduit 162 and outlet 154 and three-way valve 168 which operate substantially as in FIG. 1. The opening 164 of the conduit 162 is provided with a flow directing means to provide for more efficient mixing of the physiologically tolerable liquid with the drug entering the receiving chamber 122.

The device 110 shown in FIG. 2 is also provided with a port 170 which can be connected by a tube 180 to a reservoir of therapeutic agent. Valve means 176 can be provided to regulate the flow of therapeutic agent into the donor chamber 118.

In operation of the devices 10 and 110, the therapeutic agent is placed within the donor chamber 18 in its ionic form such as a hydrochloride salt. Generally, the agent is dispersed in a physiologically tolerable diluent such as saline. When it is desired to administer the therapeutic agent to the patient, an electromotive force is placed between the electrodes 24 and 26 such that the therapeutic agent migrates through the semipermeable membrane 26. Where electrode 26 is a cathode, a positively charged therapeutic agent will be driven through the semipermeable membrane 16 by the negative attraction of the electrode or cathode 26. The corresponding anode 24, if made of silver, will be ionized to become silver ions which react with the chloride ions to form silver chloride. The therapeutic agent which then arrives in the receiving chamber 22 can be taken up by the physiologically tolerable liquid vehicle flowing from the inlet 58 through the receiving chamber 22 and out through the outlet 54 to the patient.

The liquid vehicle preferably includes ions which correspond to those ions which do not pass through the membrane. In the case of a hydrochloride salt, the liquid vehicle includes chloride ions. Such a liquid vehicle is saline.

A still further alternative design for a device 210 according to the present invention is shown in FIG. 3. In this embodiment, both anode 224 and cathode 226 are located within donor chamber 218 which is defined by housing 228 which retains semipermeable membrane 216. The semipermeable membrane 216 is substantially impermeable to the ionic form of the therapeutic agent, but permeable to the non-ionic form of the therapeutic agent.

The membrane 216 can be made of a hydrophobic material such as silicone elastomers consisting of dimethyl and methylvinyl siloxane copolymers commercially available from Dow Chemical under the trademark Silastic. Other suitable membranes include Teflon TFE membranes (trademarks of duPont de Nemours & Co.), a styrene ethylene/butylene, styrene block copolymer with polydimethylsiloxane available under the trademark C-Flex from Concept Polymer Technologies and a polytetrafluoroethylene available under the trademark Gore-Tex from W. L. Gore & Associates, Inc.

In the embodiment shown in FIG. 3, the power source means, in this case a battery 274, and the control means, shown as a microprocessor 276, are mounted on the housing 228 to permit implantation of the entire device 210. The housing 228 and membrane 216 are also adapted for implantation into a living patient's body such as in the abdomen. A septum 278 and needle stop 282 are also provided to permit the supply of therapeutic agent to the donor chamber 218. When the device 210 is implanted, its supply of agent can be replenished through the patient's skin by a needle which extends through the septum 278.

In operation, the therapeutic agent is placed within the donor chamber 218 in its ionic form. The membrane 216 being hydrophobic resists the passage of ions. When an electromotive force is placed between the anode 224 and cathode 226, a current flows between them and the therapeutic agent is reduced to its non-ionic form. In its non-ionic form, the therapeutic agent can pass through the semipermeable membrane 216.

Since the therapeutic agent leaving the semipermeable membrane 216 is in a non-ionic form, it should be of a type which remains soluble in its nonionic form. Such therapeutic agents include hormones and the drugs phenobarbital sodium and doxorubicin.

The embodiment shown in FIG. 10 illustrates a therapeutic agent delivery system 310 of this invention generally suitable for delivering reconstituted therapeutic agent, and for sustaining release of medication as an alternate to current techniques of using drug bags in a piggyback arrangement. The device shown in FIG. 10 is substantially similar to the embodiment of FIG. 1, in that the portion of donor chamber 318 defined by semipermeable membrane 316 is located within receiving chamber 322, and first electrode 324 and second electrode 326 are similarly positioned.

However, this embodiment is provided with a removable therapeutic agent reservoir 334. Reservoir 334 has two openings, a first opening 334a and a second opening 334b, and is shown in position for use with the first opening 334a adapted for and mounted in fluid communication with the donor chamber 316 and with the second opening 334b adapted for and mounted in fluid communication with the removable container 338.

In this embodiment, the reservoir 334, prior to use, is supplied with reconstitutable drug D in substantially solid form, such as a powder. Drug D is retained in the drug reservoir 334 by sealing first the opening 334a with removable first sealing means (not shown) and sealing the second opening 334b with puncturable second sealing means 334c. Additionally, the first opening 334a and the second opening 334b are each provided with a spiked end opening to simplify mounting reservoir 334 in fluid communication with the donor chamber 318 and with container 338 for reconstitution and use, as described below.

Container 338 can be supplied with physiologically tolerable liquid L such as water, saline or dextrose and kept sterile until needed with a temporary or puncturable sealing means 340, such as a membrane, preferably located in a septum 342, including piercing means 344 located within container 338.

To reconstitute drug D, the second opening 334b is mated with the container 338 such that the sealing means 340 is punctured by the spiked end opening of the second opening 334b of the drug reservoir 334 and associated piercing means 344 pierces the second sealing means 334c thereby placing the drug reservoir 334 in fluid communication with the container 338. Thus a portion or all of drug D can be dispersed in the container 338 as by rotating the reservoir 334 and the container 338 in unison to substantially disperse the drug D in liquid L to provide reconstituted therapeutic agent RD.

The piercing means 344 is preferably located within the container 338 generally associated with the septum 342 and constructed of sufficiently rigid chemically unreactive material to pierce the sealing means 334c without interfering with fluid communication. In the embodiment shown in FIG. 10, the piercing means 344 is also preferably sufficiently flexible to be repositioned by the second opening 334b as by twisting the spiked end of the second opening 334b after contact with the piercing means 344 to push the piercing means aside.

An advantage of the embodiment shown in FIG. 10 is that reconstituted therapeutic agent RD can be retained in sterile condition by leaving the drug reservoir 334 in fluid communication with the container 338 and keeping the first opening 334a sealed until needed. For delivering reconstituted therapeutic agent RD to a patient, the first opening 334a is unsealed (removable first sealing means not shown) and mounted in fluid communication with the donor chamber 318 from where it migrates to the receiving chamber 322 in response to a driving electromotive force substantially as generally described above for the embodiment in FIG. 1 by connecting the leads 346 and 348 to an appropriate power supply source 372.

In a preferred embodiment shown in FIG. 11, the therapeutic agent delivery system or device 410 is configured in disc shape and shown in perspective view. Device 410 comprises a first housing 428 defining a donor chamber 418 adapted to receive therapeutic agent, a second housing 432 defining a receiving chamber 422 and a semipermeable membrane 416 retained between the first housing 428 and the second housing 432. The semipermeable membrane 416 is in fluid communication with and partially defines the donor chamber 418 and the receiving chamber 422.

The membrane 416 is captured between the first housing 428 and the second housing 432 by ridges on the respective housings which contact and grip the membrane when the housings are connected. The housings are preferably connected by sonic welding. In such a case, the housings are made of a suitable plastic material. It has been found that a circular shape for the membrane 416 provides the best seal with the respective housings.

A first electrode 424 is located within the donor chamber 418 immediately adjacent and above the membrane 416 and a second electrode 426 is located within the receiving chamber 422 immediately adjacent and below the membrane 416. As shown, the electrodes 424 and 426 are connected by leads 444 and 446 to an operating unit 472 including a power source means and a control means.

The device 410 is provided with an inlet port 470 through which drug D can be introduced by connecting the inlet port with a reservoir 438, such as a syringe, medicine vial, or infusion source tube containing therapeutic agent D. The port 470 can be provided with a luer-type fitting or with a spike for adapting it to reservoir 438. The device 410 is further provided with a vent 480 in communication with the donor chamber 418 including hydrophobic medium 482 that seals the vent. The hydrophobic medium is liquid impermeable and air permeable.

The receiving chamber 422 is provided with an inlet 458 and an outlet 454 through which physiologically tolerable liquid vehicle such as saline can flow to receive and carry therapeutic agent for delivery to a patient. Preferably outlet 454 is positioned in elevated lateral relationship to the inlet 458 and is of generally smaller internal diameter than the inlet. In such a case the membrane is angularly sloped.

The device 410 is preferably composed of sterilizable, non-toxic, non-reactive and disposable material for one-time use. Particularly preferred is an acrylic material, a material having the trade designation CRYOLITE, sold under the trademark G20 HIFLO by Cryo Industries of Connecticut. This material is approved for medical application by the Food and Drug Association and can be sterilized by steam autoclave or ethylene oxide.

An alternative design for the first housing 428 of device 410 is shown in top view in FIG. 12. In this design, the first housing 528 includes septa 529 to define a multiplicity of donor chambers and includes a multiplicity of electrodes so that one electrode is within each chamber. The septa 529 can be molded with the remainder of the first housing 528 and seal with the membrane 516 to define a plurality of chambers. Illustrated in FIG. 12 is one preferred embodiment having three chambers 518a, 518b, 518c, each chamber having an electrode 524a, 524b, 524c, and each chamber provided with port 570a, 570b, 570c for introducing therapeutic agent.

Accordingly, each donor chamber can retain a different therapeutic agent, D-1, D-2 and D-3, to be delivered serially, sequentially or simultaneously. For this purpose, leads 526a, 526b, 526c are connected to a power source (not shown) and can be controlled separately. The embodiment as shown in FIG. 12 has equally divided donor chambers. The volume capacity of each chamber can be the same or different as desired. Similarly, the inlet ports 570a, 570b, 570c, can each be adapted for connection to dissimilar drug reservoirs, such as a hypodermic syringe, an infusion source tube and a vial. Each chamber has one identified vent 580a, 580b and 580c associated therewith, each vent similarly sealed with hydrophobic media 582a, 582b and 582c. This particular design has the advantage of only requiring a single membrane to separately deliver a plurality of drugs. In this embodiment, the placement of membrane 516, receiving chamber 526 and its associated inlet 558 and outlet 554 (shown in ghost line) is substantially as before. Thus all donor chambers share a common receiving chamber.

As in prior embodiments, the therapeutic agent is retained by each donor chamber in FIG. 12 until an electromotive force of sufficient amount is applied between at least one of the first electrodes 524a, 524b, 524c, and the second electrode 526 to drive at least a portion of therapeutic agent, D-1, D-2, D-3, across the membrane 516 to pass from its associated donor chamber to the common receiving chamber 522. When electromotive force is no longer applied between any one of an anode or cathode, no further therapeutic agent passes or migrates through to receiving chamber 522. If desired, electrodiffusion of the drug from one or more donor chambers can be achieved by applying an electromotive force to one or more of their electrodes simultaneously, serially or sequentially.

In an alternative embodiment, the device of FIG. 11 is constructed such that the first housing 428 and the second housing 432 can be separated for interchanging the first housing 428 with the first housing 528 of FIG. 12. Alternatively, a protective sterile temporary cover may be placed over the second housing 422 of FIG. 11 until medication is needed or while donor chambers are exchanged.

For convenience, the membrane in the embodiments of FIGS. 11-12 can be separable from or incorporated with either the second housing or the first housing. However, it is preferably captured between the housings. Thus, the receiving chamber can be left in position for delivery of primary therapeutic agent liquid, such as intravenous fluid, and medication piggybacked as required with no discomfort to the patient.

FIG. 13 shows an alternative design for a vertical disc shaped device 610 in which the first housing 628 and second housing 622 are constructed so that the donor chamber 618 and its associated vent 680 is positioned in parallel and vertical relationship with the receiving chamber 638 separated by the membrane 616. In this embodiment, an interlocking ridge 685 contacts and grips the membrane 616 when the housings are connected. The membrane is captured between the housings by the ridge 685 which is received in a groove 687 defined by the second housing 622. The ridge is made about 0.015 inches (0.38 mm) high and the groove 687 about 0.007 inches (0.18 mm) deep. The housings are pressed together with the membrane in between and held by the ridge and groove and the housings are sonically welded together. The vent 680 is sealed with hydrophobic medium 682.

The inlet port 670 of the donor chamber 618 is provided with a luer-type fitting, as in the inlet 658 of the receiving chamber 638. In this embodiment, the outlet 652 of the receiving chamber is provided with a delivery means 654 for connection to standard tubing (not shown).

A first electrode 624 is exposed in the donor chamber 628 and a second electrode 626 is exposed within the receiving chamber 638, and are connected by leads to an operating unit (not shown) including a power source means and a control means.

A preferred disc-shaped device of the type shown in FIGS. 11-13 can be configured to have an overall dimensional size of about 2 inches diameter and 1.75 inches thick and a net weight of about 16.8 grams. Preferably the membrane is inherently hydrophilic and has its surface charge modified to give it a relatively high positive zeta potential over a broad pH range from 3 to 10 or a negative zeta potential, and not have any measurable effect on the surface tension of water, alcohol or other liquid passed through it and should not affect the pH value of the therapeutic agent or change its composition. A particularly preferred membrane for use with positively charged injectable drugs in solution is Carboxydyne membrane previously described.

The device 410 of FIG. 11 is designed to work as a stand alone administration device or in conjunction with a flow control unit. For use, the device 410 is first primed by passing primary liquid fluid through the receiving chamber 426 to purge it of air while the donor chamber 418 is empty. In one preferred embodiment therapeutic agent can be introduced into the donor chamber 418 by means of vented pre-filled syringe, such as sold by Becton, Dickinson and Company, Franklin Lakes, N.J., under the trademark ADD-VENT.

The therapeutic agent is preferably an ionizable drug which can be supplied as a pharmaceutically acceptable salt. The term "pharmaceutically acceptable salt" refers to the nontoxic alkali metal, alkaline earth metal and ammonium salts commonly used in the pharmaceutical industry including the sodium, potassium, lithium, calcium, magnesium, and ammonium salts and the like which are prepared by methods well known in the art. The term also includes non-toxic acid addition salts which are generally prepared by reacting the compounds of this invention with a suitable organic or inorganic acid. Representative salts include the hydrochloride, hydrobromide, sulfate, bisulfate, sulfonate, acetate, oxalate, valerate, oleate, laurate, borate, benzoate, lactate, phosphate, tosylate, citrate, barbital, maleate, fumarate, succinate, tartrate, and the like.

A wide range of drugs are available as pharmaceutically acceptable salts, and particularly as hydrochloride salts. These include aminophylline hydrochloride, doxorubicin hydrochloride, clonidine hydrochloride, dopamine hydrochloride, lidocaine hydrochloride, naloxone hydrochloride, nalorphine hydrochloride, morphine hydrochloride, morphine sulfate U.S.P., and bretylium tosylate. Simple compounds such as used to provide electrolytes to a patient including potassium chloride and ammonium chloride can also be administered by the present invention.

Where the drug or hormone cannot be placed in an ionic form, or it is not desirable to place the drug or hormone in an ionic form, the therapeutic agent can include the drug or hormone coupled to an appropriate carrier which does have an ionic form. This is particularly useful for hormones such as insulin. Such appropriate carriers include the pyridine compounds. These compounds include a heterocyclic ring having a nitrogen which can form a quaternary amine salt when oxidized. See generally, Eisner et al., *The Chemistry of Dihydropyridines*, Chemical Reviews 72: 1-42 (1972). Such pyridinium salt-drug compounds have the general formula of:

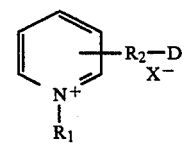

wherein $R_1$ is generally a lower alkyl group ($C_1$-$C_4$) such as methyl or ethyl, D is an active agent such as a drug or hormone, $R_2$ is a coupling agent for linking the salt to the active agent D, such as $CH_2O$, COO, or CH=NO, and $X^-$ is an anion. For example, where the drug has an amine group that is used to couple it with the carrier, the coupling agent $R_2$ is usually COO to form a carbodiimide coupling. Pyridine can be reacted with an alkyl halide such as methyl chloride to form the quaternary ammonium salt desired such as N-methylpyridinium chloride. See for example, Bodor, et al. *Journal of Pharmaceutical Sciences* 67: 685–687 (1978) and Bodor, et al. *Science,* 214: 1370–1372 (1981). See also U.S. Pat. Nos. 3,929,813 and 3,962,447 to Higuchi, et al., all incorporated by reference.

One suitable carrier 1-methylpyridinium-2-aldoxime chloride also known as 2-PAM chloride can be used in its chloride salt form and coupled to an active agent D as shown below.

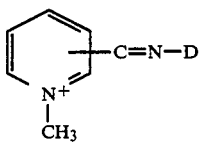

It should be understood that numerous other compounds can be used as carriers, the primary criteria being the existence of an ionic form and being physiologically tolerable.

EXAMPLE 1

This example shows the controlled release of doxorubicin hydrochloride. A perfluorosulfonic acid polymer membrane obtained from Cole-Parmer under the trademark Spectra/POR was used as the semipermeable membrane. The membrane was 42 millimeters in diameter and had a filtration area which was exposed to the donor and receiving chamber of 10.5 square centimeters. The donor chamber had a volume of 140 cubic centimeters and the receiving chamber had a volume of 37.4 cubic centimeters.

The anode was a silver wire 1.5 millimeters in diameter, 18.4 centimeters in length and wound into a spiral about a glass rod. The cathode was a platinum wire having a diameter of 0.85 millimeters and a length of 24.5 centimeters also wound around a glass rod. The anode was located within the donor chamber and the cathode within the receiving chamber.

Doxorubicin hydrochloride, also known as adriamycin hydrochloride, was prepared in a saline solution to a concentration of 0.05 milligrams/milliliter. The solution was prepared by weighing 5.0 milligrams of doxorubicin hydrochloride and placing it into a 100 milliliter volumetric flask. About 50 milliliters of 0.9 percent NaCl solution were added to the flask which was then shaken well and sonicated for five minutes. The solution was then made up to 100 milliliter volume with additional 0.9 percent NaCl solution. This solution had a pH value of 6.38. Its ultraviolet (UV) spectrum was measured using a Perkin-Elmer Lambda 3 UV/Visual Spectrophotometer at wavelengths of 494, 477, 265, 249, 230, and 202 nanometers. This spectrum was used as a reference to show the drug remained unchanged after it had passed through the membrane.

Using a pipette, 50 milliliters of the solution was placed within the donor chamber. As the study continued, additional solution was added from a reservoir to maintain the donor chamber level 3 centimeters above the receiving chamber level. The liquid level in the donor chamber was 3 centimeters higher than the level in the receiving chamber. The anode was connected to the positive pole and the cathode to the negative pole of a power supply which used a six volt battery. At first, the power was left off and a saline solution was passed through the receiving chamber at a flow rate of 100 milliliters per hour. The effluent was collected using a fraction collector programmed to collect up to a 50 milliliter sample every 30 minutes in separate test tubes. The effluent from the receiving chamber was collected for 24 hours and the presence of doxorubicin hydrochloride in the effluent was determined using high performance liquid chromatography (HPLC).

The chromatography column was a C18 duPont Zorbax column 24 centimeters long, with a 4.6 millimeter internal diameter and a 10 micrometer particle size. The mobile phase was a 96.2 percent 2-propanol and 3.8 percent of 0.5 Molar (M) sodium acetate buffer solution (pH 4.5). The flow rate was 2 milliliters per minute at a pressure of 1600 pounds per square inch. The retention time of the doxorubicin hydrochloride peak was found to be 12.5 minutes.

The detector used was a Spectra Physics fixed wavelength detector set at a wavelength of 254 nanometers. A Valco Instrument Co. injector having a manual injection port with loop of 50 microliters was used with an L.D.C. HPLC pump.

A series of calibration solutions of this particular drug were prepared with concentrations of 0.1, 0.2, 0.5, 1.0, 2.0, 3.0, 5.0, 7.0, 8.0, 9.0, 10.0, 15.0 and 20.0 milligrams/milliliter. Each calibration solution was injected into the HPLC system and the corresponding peak area was obtained by a Spectra Physics SP 4100 integrator connected to the fixed wavelength detector. The plot of the peak area vs. concentration of calibration solution was used to calculate the concentration and therefore the amount of drug that had been delivered through the membrane. Peak area was found to be a linear function of concentration.

At the end of the 24 hour period with no current between the anode and the cathode, no doxorubicin was detected in the effluent. Therefore, the device does not allow the passage of therapeutic agent when there is no electromotive force between the electrodes.

After demonstrating that none of the drug passed through the membrane when the power was off, the power was then set at 6.00 volts and a current of 0.31 milliamps. A slight trace of doxorubicin could be seen in the receiving chamber because of its orange color. The HPLC chromatograms indicated that the effluent contained doxorubicin with the same retention time of 12.5 minutes as that of the starting material and that the ultraviolet and visible spectra also showed identical maximum peaks at 494, 477, 264, 269, 230, and 202 nanometers. This indicates there was no chemical change in the drug as it passed through the device.

The experiment was performed for 36 hours with four test tubes being pooled together to represent an average solution collected every two hours. The amount of the drug in milligrams was measured by the fixed wavelength detector and converted from curve area to milligrams by referring to the calibration curve described above. The results were plotted as a function of time and are shown in FIG. 4 (straight D.C. mode). As can be seen, the total amount of drug which had passed through the membrane by any given time was substantially linear with time for constant voltage and current.

Next the delivery of the drug as a function of the current was examined. For each given current, the study was carried out for a period of two hours and the amount of doxorubicin hydrochloride was determined as described above. The results as measured by the peak area under each curve are plotted in FIG. 5 (straight D.C. mode). As can be seen from FIG. 5, the amount of drug released is directly proportion to the current between the anode and the cathode. This is a zero order profile. The slope of the lines shown in FIGS. 4 and 5 can be used as a standard calibration for doxorubicin hydrochloride and the particular membrane used. The slope, however, will be different for different drugs and different membranes.

EXAMPLE 2

The examinations of Example 1 were repeated except the drug lidocaine hydrochloride was prepared in a solution of 10 milligrams/milliliter using the same technique described above. The device and protocol used was the same as in Example 1.

The HPLC system was a Whatman C8 column, 15 centimeters long by 4.6 millimeter internal diameter. The mobile phase was 55 percent acetonitrile and 45 percent 0.1M sodium acetate buffer solution (pH 4.5). The flow rate was 2 milliliters per minute at a pressure of 1200 pounds per square inch. The retention time of the lidocaine hydrochloride peak was found to be 8.5 minutes. UV spectroscopic measurements were made with the same equipment as in Example 1 at wavelengths of 210.2 and 240.0 nanometers. The lidocaine hydrochloride in the effluent was checked using HPLC and the retention time and UV spectrum remained the same. Therefore, the drug did not undergo any change as it passed through the membrane.

The amount of lidocaine hydrochloride in the effluent was measured using the fixed wavelength detector and integrator as in Example 1. A plot of peak area vs. concentration was similarly prepared. As can be seen by the results in FIG. 6 (straight D.C. mode), the amount of lidocaine hydrochloride passing through the membrane is a linear function of time with a constant voltage of 6.0 volts and current of 0.31 milliamps.

Similar to Example 1, the amount of lidocaine hydrochloride passing through the membrane as a function of current was also examined. As in Example 1, the test was for two-hour periods for each current. The results as measured by the peak area output of the integrator are shown in FIG. 7 (straight D.C. mode). The delivery rate of lidocaine hydrochloride is thus also a linear function of the current.

EXAMPLE 3

This example examined the use of the device with the drug clonidine hydrochloride. A clonidine hydrochloride solution of 0.10 milligrams/milliliter was prepared using the same technique described above. The device and protocol used was the same as in Example 1.

The HPLC column was the same as in Example 2. The mobile phase was 65 percent methanol and 35 percent 0.1M sodium acetate buffer solution (pH 4.0). The flow rate was 2 milliliters per minute at a pressure of 1300 pounds per square inch. The retention time for clonidine hydrochloride peak was 5.7 minutes. UV spectroscopic measurements were made at wavelengths of 210 and 252 manometers with the same equipment as in Example 1. The retention times with spectroscopic measurements remained the same after the drug passed through the membrane.

The amount of clonidine hydrochloride in the effluent was measured using the fixed wavelength detector and integrator as in Example 1. A plot of peak area vs. concentration was similarly prepared. As can be seen in FIG. 8, for a constant voltage of 6.0 volts and a current of 0.31 milliamperes, the amount of clonidine hydrochloride in the effluent was a linear function with time.

Figure 9:
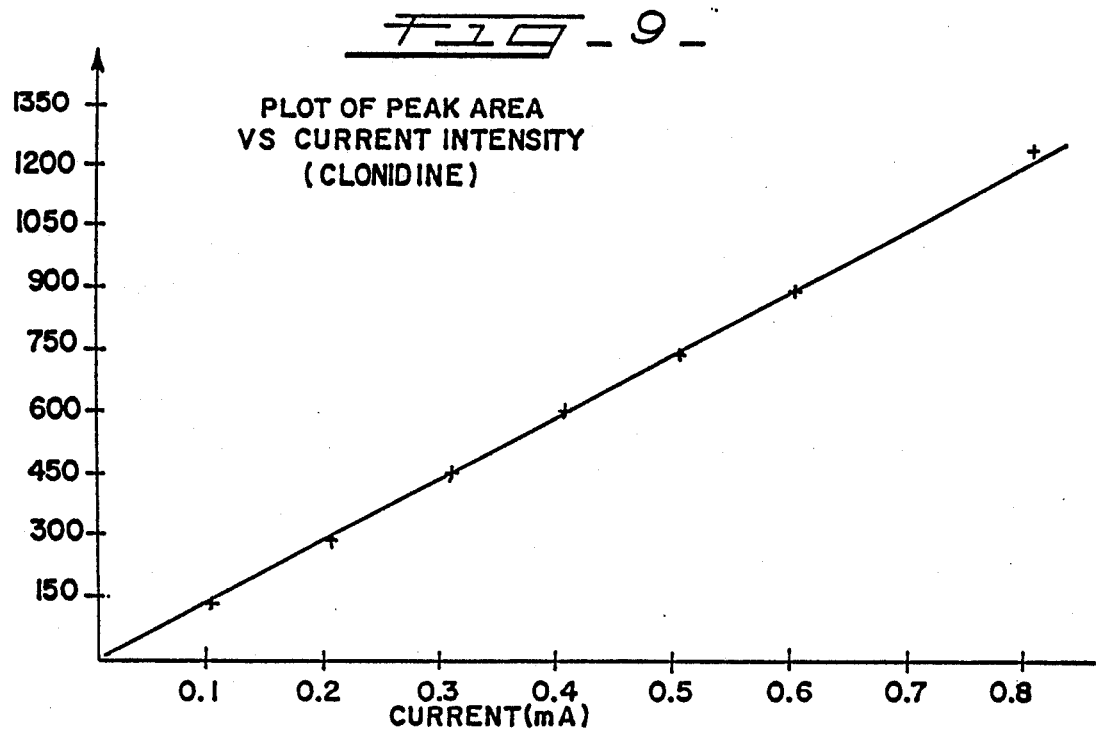

The amount of clonidine hydrochloride in the effluent as a function of current was measured by peak area as described above. As can be seen in FIG. 9, the amount of clonidine hydrochloride in the effluent for each two-hour period was also a linear function of current.

EXAMPLE 4

This example shows the controlled release of aminophylline hydrochloride from a disc-shaped therapeutic agent delivery system of the type generally shown in FIG. 11. A negatively charged membrane obtained from Pall Biosupport Division under the trademark Carboxydyne in a pore size rating of 0.2 micrometers and in disc form was used as the semipermeable membrane. The membrane was sized to fit the disc-shaped device which was 2 inches in diameter and had a filtration surface exposed to the donor chamber and the receiving chamber.

The volume of the donor chamber was 15 milliliters and the receiving chamber was 5 milliliters. The anode was located in the donor chamber and the cathode was located in the receiving chamber.

The receiving chamber was primed with a primary fluid intravenous (iv) injection liquid, such as 0.9 percent USP grade NaCl in water or 5 percent USP grade dextrose in water, to purge the air from the chamber, the inlet was attached to the iv tubing and the drop rate was adjusted with a flow regulator, such as Master-flow to give a flow rate effluent of 1 milliliter/minute from the outlet.

The donor chamber was equipped with a spiked port for fitting to a standard drug vial. For convenience, a single dose unit of USP grade aminophylline hydrochloride injection liquid (pH 8.6–9.0) obtained from LyphoMed of Melrose Park, Ill. was used. The vial contained 500 milligrams drug in 20 milliliters volume. The anode and cathode were connected to a control current source power supply (Model 225 Keithley) and the current set to each of the following values for 30 minutes: 10 microAmperes, 50 microAmperes, 250 microAmperes, 500 microAmperes and 1 milliAmpere. The voltage varied between 0.05 to 3 volts. The effluent from the receiving chamber was collected every 5 minutes using a Haake Buchler Model LC 100 fraction collector.

The effect of current applied on the rate of drug released was determined by analyzing the collected fractions by HPLC. The HPLC system consisted of a Waters 600 Four Solvent Delivery System, Waters Autosampler Wisp 712, Waters 990 Photodiode Array Detector, Waters 740 Data Module, NEC Computer 20 Megabytes Model APC III, and Waters 990 Plotter. The chromatography column was a reversed phase duPont Zorbax column 25 centimeters long, with a 1.5 millimeter internal diameter and a 10 micrometer particle size. The mobile phase was 35 percent acetonitrile and 65 percent of 0.035 Molar triethylammonium acetate buffer (pH 4.6). The flow rate was 1.5 milliliters per minute at an average pressure of 1100 p.s.i. The detector was set at a wavelength of 254 nanometers.

A comparison of a chromatogram and pH of the aminophylline hydrochloride recovered against that of a standard solution showed that the aminophylline was not changed by passing through the membrane. The total amount of aminophylline hydrochloride recovered was 475.5 milligram i.e., 95.1 percent of starting amount was delivered.

Figure 14:
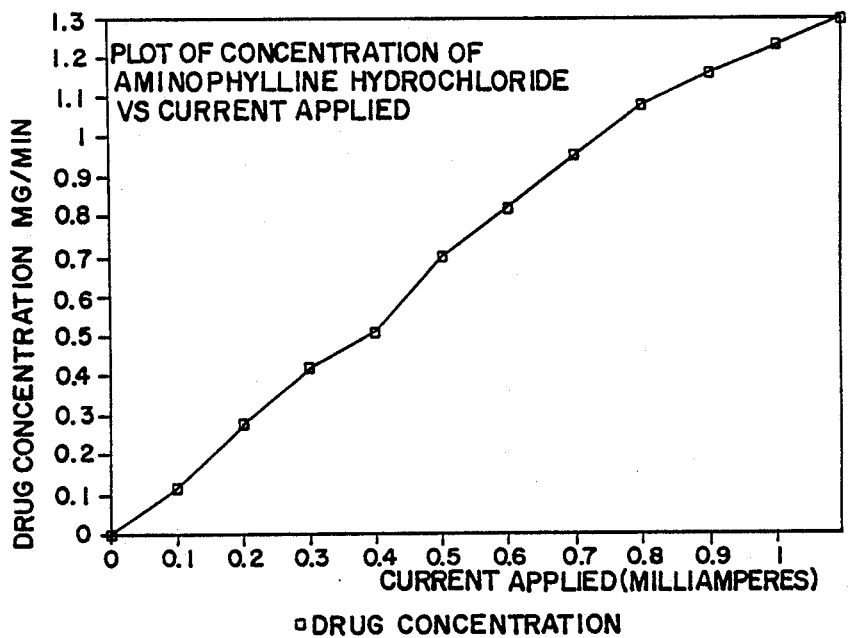

The milligrams of drug released per minute was plotted against current applied over a range of 0.1 to 1.3 milliAmperes is summarized in FIG. 14. As can be seen in FIG. 14, the amount of aminophylline hydrochloride released was directly proportional to the amount of current applied between the anode and cathode.

EXAMPLE 5

This example illustrates a typical pattern of aminophylline hydrochloride administration when a therapeutic dosage and a maintenance dosage is delivered over a period of about 90 minutes from the disc-shaped device described in Example 4. In this example, the procedure of Example 4 was followed except that a current of 1 milliampere was applied to provide a loading dose of about 14.3 milligrams/milliliter over a 25 minute administration period using a primary fluid flow of 1 milliliter/minute.

This loading dosage was calculated to approximate the therapeutic range for a 60 kilogram (kg) patient, based on 6 milligrams/kg or 360 milligrams/60 kg patient not already receiving theophylline, with a maintenance dose varying from 0.1 to 1.2 milligrams/kg depending on the patient's condition and needs. During this administration period a total of 367.5 milligrams of drug were delivered.

Figure 15:
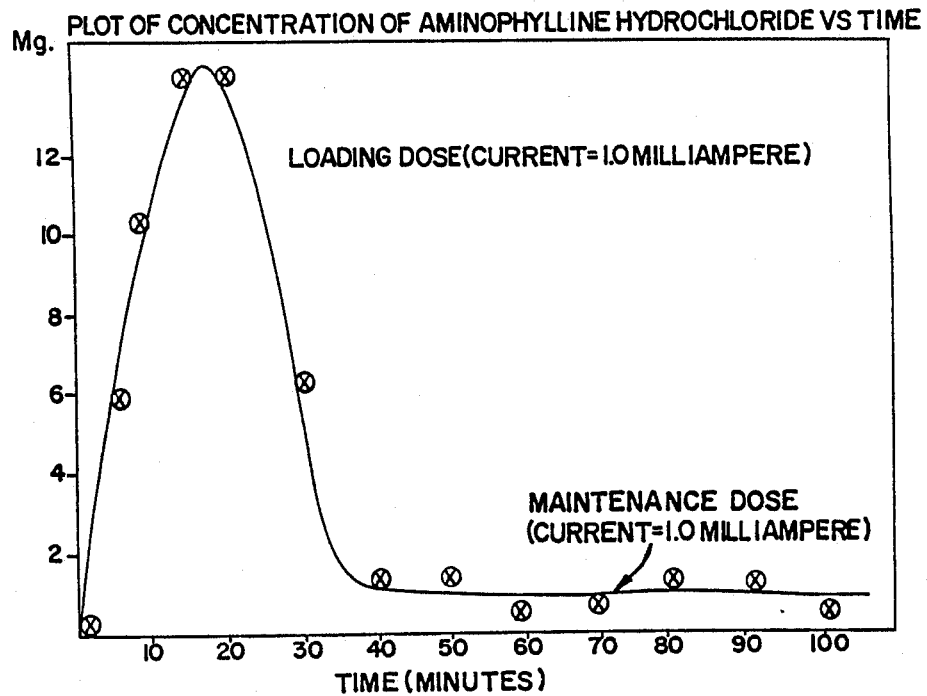

After that period, the current was adjusted to 0.10 milliAmpere to provide a maintenance dose of about 1.2 milligrams/minute or 1.2 milligrams/kg/hour for an additional period of about 75 minutes. The amount of drug delivered plotted against time of delivery is summarized in FIG. 15. As shown, delivery was sustained and satisfactory.

EXAMPLE 6

The examinations of Example 4 were repeated using the same device, except the drug doxorubicin hydrochloride was reconstituted for use and the flow rate of the primary fluid was 2 milliliters/minute.

Doxorubicin hydrochloride standard material was obtained from Aldrich Chemical in 10 milligram vials. The drug was reconstituted to a concentration of 1 milligram/milliliter by dispersing 10 milligrams of doxorubicin hydrochloride in 10 milliliters of sterile water contained in a reservoir of 15 milliliter capacity. For this study, the reservoir was a vial mounted on the donor chamber and replaced as needed so that a total single unit dose of 30 milligrams drug were used.

The HPLC protocol of Example 4 was generally followed, except the chromatography column used was a Whatman C-18 column, 25 centimeters long, with a 1.5 millimeter internal diameter and a 10 micrometer particle size, and the mobile phase was 80 percent acetonitrile and 20 percent 0.035 Molar triethylammonium acetate buffer (pH 4.6) at a flow rate of 2 milliliters/minute with the detector set at 262 nanometers.

A comparison of the HPLC chromatogram and pH of the effluent drug with that of a standard solution at the same concentration showed them to be identical. Thus the doxorubicin hydrochloride was not changed after passing through the membrane. The total amount of doxorubicin hydrochloride recovered was 28.2 milligrams or 94 percent of starting amount.

The effect of current applied plotted against the milligrams of drug released/minute is shown in FIG. 16. As shown in FIG. 16, the rate of drug delivery reached a plateau at a current of about 200 microAmpere. A range for current levels of about 50 microAmperes to about 250 microAmperes was judged sufficient to deliver therapeutic concentrations within amounts suggested for intravenous dosage.

EXAMPLE 7

The pattern of delivering a dosage of 30 milligrams doxorubicin hydrochloride by the therapeutic agent delivery method of the invention using the device of Example 4 was compared against that achieved by conventional intravenous bolus injection method and that achieved by conventional minibag infusion pump method.

For this comparison, the device of Example 4 was used and a current of 250 microAmperes was applied. The sample was reconstituted as using the protocol in Example 6. The milligrams doxorubicin hydrochloride/milliliters delivered plotted against administration time is shown in FIG. 17.

The results show that the pattern for delivering doxorubicin hydrochloride by the therapeutic agent delivery method of this invention using the device of Example 4 falls between that of a conventional i.v. bolus push and that of a conventional minibag infusion pump method. As seen in FIG. 17, the milligrams of doxoribicin hydrochloride delivered by electrodiffusion technique using the device of this invention reached a level of about 1.4 milligrams/milliliter relatively quickly (within 5 minutes) and this level was sustained over an additional period of about 20 minutes. Delivery of a 30 milligrams dose was substantially complete within a period of about half an hour. The conventional minibag infusion, pump on the other hand, took almost three times longer to reach and sustain a lower level of 1 milligram/milliliter and, hence, took nearly twice as long to deliver 30 milligrams of doxorubicin.

EXAMPLE 8

The examination of Example 4 was repeated except that 200 milligrams of the drug dopamine hydrochloride were delivered from a 5 milliliter capacity vial at a drug concentration of 40 milligrams/milliliter, and the effluent flow rate of the primary fluid was set at 2 milliliters/minute. No dilution of the drug was necessary prior to introducing it to the donor chamber of the device of Example 4 as the amount of drug released was maintained within a range of about 0.8 to 1.6 milligrams/milliliter by adjusting amperage between the electrodes.

The analytical protocol of Example 4 was repeated except that the HPLC column was the same as Example 6.

Figure 18:
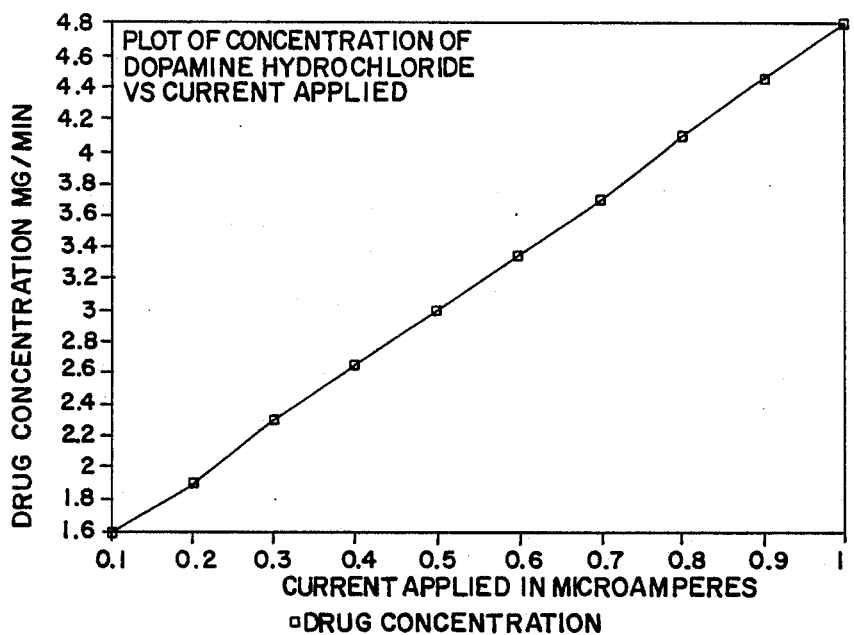

The milligrams/minute dopamine hydrochloride delivered plotted as a function of current applied ranging from 0.1 to 1.0 microAmpere is shown in FIG. 18 and shows that the amount of drug in the effluent was a linear function of current applied.

A comparison of the HPLC chromatogram of the recovered drug against a standard showed that dopamine hydrochloride was not changed by passing it through the membrane. A total of 193.2 milligrams of drug were recovered, i.e., 96.6 percent of starting amount was delivered.

EXAMPLE 9

The pattern of delivery of a dosage of 200 milligrams of dopamine hydrochloride using the device of Example 4 and method of delivery protocol of Example 8 was examined at three applied current levels, 100 microAmperes, 250 microAmperes, and 500 microAmperes. The results were also compared against the pattern of delivery obtained from a conventional infusion pump method also set for delivering 2 milliliters/minute.

Figure 19:
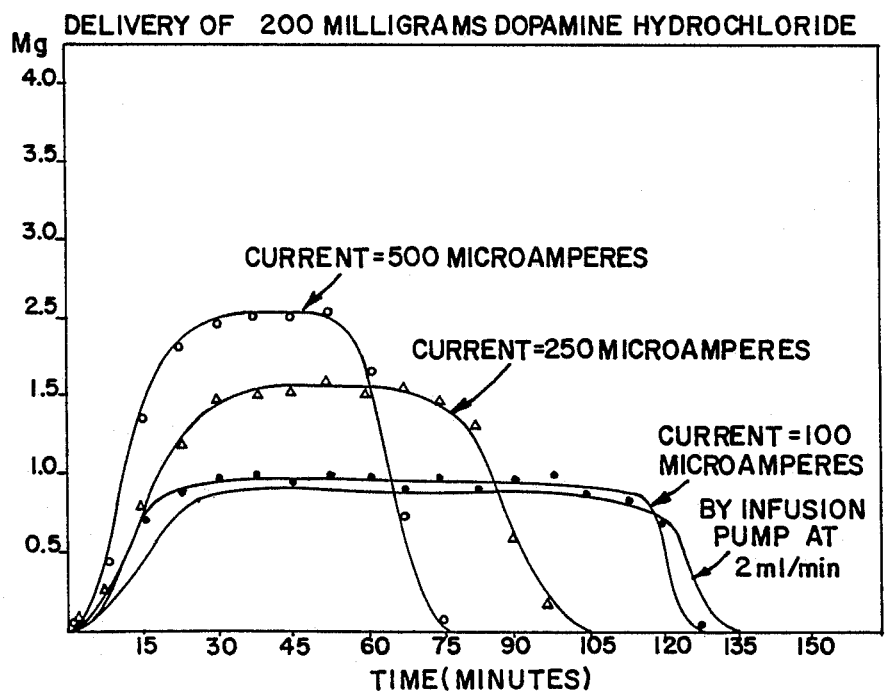

A comparison of the milligrams of dopamine hydrochloride delivered plotted against time is summarized in FIG. 19. As seen in FIG. 19, the delivery of drug from the therapeutic agent system and method of this invention using an electromotive force of 100 microAmperes was substantially comparable to that of a conventional infusion pump method in the amount of drug delivered and in delivery time. As the intensity of the current increased, the amount of drug delivered increased thereby shortening delivery time, a result consistent with earlier findings.

As can be seen from the above examples, therefore, the amount and rate of therapeutic agent delivery is a linear function of time and current between the electrodes. This simplifies the controlled administration of the agent to the patient. In addition, it has been found that the use of a pulsed or voicing D.C. wave will provide increased drug flow. For example a D.C. pulse wave (a square wave with only positive and zero volumes) having an on/off ratio of 4/1 at a frequency of 1000 Hertz and maximum current of 0.31 mA it is possible to obtain increased deliveries of drugs such as doxorubicin hydrochloride and lidocaine hydrochloride. This can be seen in FIGS. 4–7 by the D.C. Pulse form plot corresponding to examinations discussed in Examples 1 and 2.

It will be understood that numerous other drugs or drug carrier systems can also be used as a therapeutic agent with the present invention.

What is claimed is:

1. A therapeutic agent delivery system comprising:
   (a) a first housing;
   (b) a second housing mounted on the first housing, and having an inlet and an outlet;
   (c) a semipermeable membrane captured between the first housing and the second housing, the membrane and first housing defining a donor chamber adapted to receive a therapeutic agent and the membrane and the second housing defining a receiving chamber in fluid communication with the inlet and the outlet and being adapted to receive therapeutic agent from the donor chamber through the membrane;
   (d) a first electrode exposed within the donor chamber; and
   (e) a second electrode exposed within the receiving chamber such that the therapeutic agent remains in the donor chamber until an electromotive force of a sufficient amount is applied between the electrodes whereby at least a portion of the therapeutic agent passes from the donor chamber to the receiving chamber and when the electromotive force is no longer applied no further therapeutic agent is delivered to the receiving chamber.

2. The therapeutic agent delivery system of claim 1 further including delivery means associated with the outlet for delivering the therapeutic agent from the receiving chamber to a patient.

3. The therapeutic agent delivery system of claim 1, wherein the housing includes at least one inlet port on the first housing in fluid communication with the donor chamber.

4. The therapeutic agent delivery system of claim 1, including a vent on the first housing in communication with the donor chamber, the vent including an air permeable hydrophobic sealing means.

5. The therapeutic agent delivery system of claim 3 further including a therapeutic agent reservoir releasably mounted on the port in fluid communication with at least the one donor chamber.

6. The therapeutic agent delivery system of claim 1, wherein the first housing includes at least one septum integrally mounted in contact with and in sealing cooperation with the membrane and the housing to define at least two donor chambers, each donor chamber having an electrode exposed within.

7. The therapeutic agent delivery system of claim 1 wherein the first electrode is an anode and the second electrode is a cathode.

8. The therapeutic agent delivery system of claim 1 wherein the membrane is made of material that is ion selective.

9. The therapeutic agent delivery system of claim 8 wherein the membrane is made of hydrophilic polymer having its surface charge modified.

10. The therapeutic agent delivery system of claim 1 including power source means for generating the electromotive force.

11. The therapeutic agent delivery system of claim 10 including control means for controlling the electromotive force generated by power source means over time.

12. A reservoir suitable for use in the therapeutic agent delivery system of claim 5, the reservoir having at least two generally opposed openings, the first opening having first sealing means removable for placing the first opening in fluid communication with the port of the one identified housing donor chamber and the second opening having second sealing means puncturable on placing the second opening in fluid communication with a removable container, the removable container retaining a portion or all of the therapeutic agent dispersed in a physiologically tolerable liquid and including piercing means for puncturing the sealing means of the second opening; such that when the second opening of the reservoir is mounted in fluid communication with the container and the first opening of the reservoir is mounted on the port, the liquid is placed in flow communication with the reservoir and passes from the reservoir to the identified donor chamber.

13. The therapeutic agent delivery system of claim 12, wherein the reservoir retains a portion or all of the therapeutic agent in powder form.

14. The therapeutic agent delivery system of claim 13, wherein the container includes part or all of the powder form therapeutic agent dispersed therein.

15. A method of reconstituting a substantially solid therapeutic agent in a therapeutic agent delivery system and administering the reconstituted therapeutic agent in a liquid form to a patient comprising the steps of:
   (a) providing a reservoir retaining the substantially solid therapeutic agent, the reservoir having a first opening and a second opening, the first opening sealed with first removable sealing means and the second opening sealed with second puncturable sealing means;

(b) providing a container retaining a physiologically tolerable liquid for dispersing the therapeutic agent and including puncturing means for the second sealing means;

(c) puncturing the second sealing means of the second opening of the reservoir by placing the second opening in communication with the container and associated puncturing means such that therapeutic agent is received in the container;

(d) rotating the reservoir and container in unison to substantially disperse the therapeutic agent in the liquid to provide reconstituted therapeutic agent;

(e) maintaining the reservoir in fluid communication with the container until the first sealing means of the first opening is removed;

(f) providing a therapeutic delivery system comprising:

(i) a first housing defining a donor chamber and having an inlet adapted to receive the therapeutic agent from the reservoir and hold the therapeutic agent in the donor chamber;

(ii) a second housing defining a receiving chamber adapted to receive the therapeutic agent from the donor chamber and having an inlet and an outlet in fluid communication with the receiving chamber;

(iii) a semipermeable membrane in fluid contact with and separating the donor chamber and the receiving chamber, the membrane being of a material which is ion selective;

(iv) a first electrode exposed within the donor chamber; and (v) a second electrode exposed within the receiving chamber such that the therapeutic agent remains in the donor chamber until an electromotive force of a sufficient amount is applied between the first and second electrodes whereby at least a portion of the therapeutic agent passes from the donor chamber to the receiving chamber;

(g) removing the sealing means from the first opening of the reservoir;

(h) placing the first opening of the reservoir in fluid communication with the donor chamber of the housing such that therapeutic agent is received and retained therein;

(i) applying an electromotive force between the first and second electrode;

(j) delivering the therapeutic agent which passes thrugh the membrane to the receiving chamber to the patient.

16. The method of claim 15 further including the step of providing power source means for generating the electromotive force.

17. The method of claim 16 further including the step of providing a control means for controlling the electromotive force generated by power source means over time.

18. A therapeutic agent delivery system for delivering a multiplicity of therapeutic agents comprising:

(a) a first housing defining a multiplicity of donor chambers, each chamber adapted to receive and hold a different therapeutic agent;

(b) a second housing defining a receiving chamber;

(c) a semipermeable membrane in fluid contact with and separating each donor chamber from the receiving chamber, the membrane being of a material which is ion selective;

(d) a multiplicity of first electrodes, each first electrode being exposed within respective donor chambers;

(e) a second electrode exposed in communication with the receiving chamber such that the therapeutic agent in each donor chamber remains in its identified chamber until electromotive force of sufficient amount of applied between at least one first electrode and the second electrode whereby at least a portion of the therapeutic agent passes from the donor chamber to the receiving chamber;

(f) an inlet on the second housing in fluid communication with the receiving chamber; and (g) an outlet on the second housing in fluid communication with the receiving chamber.

19. The therapeutic agent delivery system of claim 18 wherein the semipermeable membrane is made of a hydrophilic material having its surface charge modified to be permeable to cations but substantially impermeable to anions and each of the first electrodes is an anode and the second electrode is a cathode.

20. The therapeutic agent delivery system of claim 18 wherein the semipermeable membrane is made of a hydrophilic material having its surface charge modified to be permeable to anions but substantially impermeable to cations and each of the first electrodes is a cathode and the second electrode is an anode.

21. The therapeutic agent delivery system of claim 18 further including a multiplicity of inlet ports each in fluid communication with an identified donor chamber.

22. The therapeutic agent delivery system of claim 21 further including a vent in communication with the identified donor chamber, the vent including an air permeable, hydrophobic sealing means.

23. The therapeutic agent delivery system of claim 18 including power source means for generating the electromotive force.

24. The therapeutic agent delivery system of claim 23 including control means for controlling the electromotive force generated by power source means over time.

25. A method for controlling the administration of a multiplicity of therapeutic agents to a patient comprising the steps of:

(a) providing a housing having a semipermeable membrane defining a multiplicity of donor chambers, each donor chamber carrying a first electrode, and a common receiving chamber adapted to receive the therapeutic agent and carrying a second electrode;

(b) placing a therapeutic agent in at least one donor chamber;

(c) retaining the therapeutic agent in its identified donor chamber until an electromotive force is applied between any one of a first electrode in communication with an associated identified donor chamber and the second electrode in communication with the receiving chamber;

(d) applying an electromotive force between a first identified electrode and the second electrode such that at least a portion of the therapeutic agent migrates through the membrane into the receiving chamber and is retained when the electromotive force is not applied; and (e) delivering the migrant therapeutic agent to the patient.

26. The method of claim 25 wherein the agent passing through the membrane is delivered to the patient by a flow of a physiologically tolerable liquid.

* * * * *